United States Patent
Wada et al.

(10) Patent No.: US 10,993,972 B2
(45) Date of Patent: May 4, 2021

(54) THERAPEUTIC AGENT FOR ISCHEMIC DISEASES

(71) Applicants: Shinshu University, Matsumoto (JP); Anaeropharma Science, Inc., Tokyo (JP)

(72) Inventors: Yuko Wada, Matsumoto (JP); Yuko Shimatani, Matsumoto (JP); Takashi Yano, Tokyo (JP); Takeshi Masaki, Matsumoto (JP)

(73) Assignees: Shinshu University, Matsumoto (JP); Anaeropharma Science, Inc., Tokyo (JP)

( * ) Notice: Subject to any disclaimer, the term of this patent is extended or adjusted under 35 U.S.C. 154(b) by 808 days.

(21) Appl. No.: 15/544,565

(22) PCT Filed: Jan. 18, 2016

(86) PCT No.: PCT/JP2016/051293
§ 371 (c)(1),
(2) Date: Apr. 9, 2018

(87) PCT Pub. No.: WO2016/117508
PCT Pub. Date: Jul. 28, 2016

(65) Prior Publication Data
US 2018/0360893 A1 Dec. 20, 2018

(30) Foreign Application Priority Data
Jan. 19, 2015 (JP) .............................. JP2015-007760

(51) Int. Cl.
| | |
|---|---|
| A61K 35/745 | (2015.01) |
| A61K 47/26 | (2006.01) |
| A61K 48/00 | (2006.01) |
| C12Q 1/02 | (2006.01) |
| A61K 35/74 | (2015.01) |
| C12N 15/09 | (2006.01) |
| C12N 15/74 | (2006.01) |

(52) U.S. Cl.
CPC ............ *A61K 35/745* (2013.01); *A61K 35/74* (2013.01); *A61K 47/26* (2013.01); *A61K 48/00* (2013.01); *C12N 15/09* (2013.01); *C12N 15/746* (2013.01); *C12Q 1/02* (2013.01)

(58) Field of Classification Search
CPC ...... A61K 35/74; A61K 35/745; A61K 47/26; A61K 48/00; C12N 15/09; C12N 15/746; C12Q 1/02
USPC ...................................... 424/93.2; 435/252.3
See application file for complete search history.

(56) References Cited

U.S. PATENT DOCUMENTS

| | | | |
|---|---|---|---|
| 6,416,754 B1 | 7/2002 | Brown et al. | |
| 6,652,849 B2 | 11/2003 | Brown et al. | |
| 9,730,968 B2* | 8/2017 | Wada | A61K 35/745 |
| 2003/0103952 A1 | 6/2003 | Brown et al. | |
| 2005/0025745 A1 | 2/2005 | Fujimori et al. | |
| 2011/0110893 A1* | 5/2011 | Sasaki | A61P 9/00 424/93.2 |
| 2011/0189758 A1 | 8/2011 | Shimatani-Shibata et al. | |
| 2011/0190472 A1 | 8/2011 | Shimatani-Shibata et al. | |
| 2017/0183667 A1 | 6/2017 | Koseki et al. | |

FOREIGN PATENT DOCUMENTS

| | | |
|---|---|---|
| JP | 2002-97144 A | 4/2002 |
| JP | 2003-014734 | 1/2003 |
| WO | WO 2007/136107 A1 | 11/2007 |
| WO | WO 2011/093465 A1 | 8/2011 |
| WO | WO 2011/093468 A1 | 8/2011 |
| WO | WO 2013/008881 A9 | 1/2013 |
| WO | WO 2014/010758 A1 | 1/2014 |

OTHER PUBLICATIONS

Genbank Accession No. AAX44931.1. Fujita et al. Nov. 7, 2005.
Genbank Accession No. EPE38071.1. Oberg et al. Jun. 17, 2013.
Fujita et al., Identification and molecular cloning of a novel glycoside hydrolase family of core 1 type O-glycan-specific endo-alpha-N-acetylgalactosaminidase from Bifidobacterium longum. J Biol Chem. Nov. 11, 2005;280(45):37415-22. Epub Sep. 1, 2005.
Gomi et al., High performance system for signal peptide prediction: SOSUisignal, Chem-Bio Informatics J. 2004;4(4):142-147.
Gupta et al., Human studies of angiogenic gene therapy. Circ Res. Oct. 9, 2009;105(8):724-36. doi: 10.1161/CIRCRESAHA.109.200386.
Morishita et al., Phase I/IIa clinical trial of therapeutic angiogenesis using hepatocyte growth factor gene transfer to treat critical limb ischemia. Arterioscler Thromb Vasc Biol. Mar. 2011;31(3):713-20. doi:10.1161/ATVBAHA.110.219550. Epub Dec. 23, 2010.
Yazawa et al., Bifidobacterium longum as a delivery system for cancer gene therapy: selective localization and growth in hypoxic tumors. Cancer Gene Ther. Feb. 2000;7(2):269-74.
Yazawa et al., Bifidobacterium longum as a delivery system for gene therapy of chemically induced rat mammary tumors. Breast Cancer Res Treat. Mar. 2001;66(2):165-70.
PCT/JP2016/051293, Apr. 12, 2016, International Search Report and Written Opinion.
PCT/JP2016/051293, May 19, 2017, International Preliminary Report on Patentability.

* cited by examiner

Primary Examiner — Janet L Epps-Smith
(74) Attorney, Agent, or Firm — Wolf, Greenfield & Sacks, P.C.

(57) ABSTRACT

Provided are: a transformation plasmid for transforming anaerobes and enabling highly efficient and stable secretory expression of a target protein; a gene delivery carrier formed from said anaerobes transformed by said plasmid; a pharmaceutical composition including said gene delivery carrier; and a method for diagnosing or treating an ischemic disease utilizing these. Also provided are: a novel secretory signal; a transformation plasmid including said secretory signal; a gene delivery carrier formed from anaerobes transformed by said plasmid; a pharmaceutical composition including said gene delivery carrier; and a method for diagnosing or treating an ischemic disease utilizing these.

9 Claims, 5 Drawing Sheets

Specification includes a Sequence Listing.

Detected with anti-human FGF2 antibody

```
                        SEQUENCE LISTING

<160> NUMBER OF SEQ ID NOS: 38

<210> SEQ ID NO 1
<211> LENGTH: 29
<212> TYPE: PRT
<213> ORGANISM: Artificial Sequence
<220> FEATURE:
<223> OTHER INFORMATION: secretion signal peptide (SP56)

<400> SEQUENCE: 1

Met Lys Lys Lys Thr Ile Ser Ala Ala Leu Ala Thr Ala Leu Ala
1               5                   10                  15

Leu Thr Cys Met Gly Ser Gly Gly Gly Thr Ala Phe Ala
            20                  25

<210> SEQ ID NO 2
<211> LENGTH: 33
<212> TYPE: PRT
<213> ORGANISM: Artificial Sequence
<220> FEATURE:
<223> OTHER INFORMATION: secretion signal peptide (SP67)

<400> SEQUENCE: 2

Met Lys Ile Asn Asn Lys Gly Lys Gly Ala Leu Ile Ala Ala Ile Thr
1               5                   10                  15

Ala Ala Ala Thr Leu Leu Ser Cys Gly Leu Ala Ala Ala Ser Ala Ser
            20                  25                  30

Ala

<210> SEQ ID NO 3
<211> LENGTH: 87
<212> TYPE: DNA
<213> ORGANISM: Artificial Sequence
<220> FEATURE:
<223> OTHER INFORMATION: dna for secretion signal peptide (SP56)

<400> SEQUENCE: 3
atgaaaaaga agaagactat atcggctgcg ctggcaacag cgttagcctt aacctgcatg      60
ggcagcgggg gaggtactgc gttcgca                                          87

<210> SEQ ID NO 4
<211> LENGTH: 99
<212> TYPE: DNA
<213> ORGANISM: Artificial Sequence
<220> FEATURE:
<223> OTHER INFORMATION: dna for secretion signal peptide (SP67)

<400> SEQUENCE: 4
atgaagataa acaataaggg caagggcgct cttatcgcgg caattaccgc cgcggcaacg      60
ctattgtcat gcgggctggc cgctgcaagt gccagtgcg                             99

<210> SEQ ID NO 5
<211> LENGTH: 25
<212> TYPE: PRT
<213> ORGANISM: Artificial Sequence
```

<220> FEATURE:
<223> OTHER INFORMATION: spacer peptide

<400> SEQUENCE: 5

Val Pro Leu Ser Asp Ala Asp Leu Gln Thr Leu Ala Ser Gln Ile Gln
1               5                   10                  15

Gln Ile Asn Asp Thr Ser Asp Ser Ala
            20                  25

<210> SEQ ID NO 6
<211> LENGTH: 25
<212> TYPE: PRT
<213> ORGANISM: Artificial Sequence
<220> FEATURE:
<223> OTHER INFORMATION: spacer peptide

<400> SEQUENCE: 6

Ala Gly Val Asp Tyr Leu Pro Thr Ile Gly Gln Val Pro Thr Tyr Thr
1               5                   10                  15

Lys Phe Gln Pro Thr Ala Asp Pro Gly
            20                  25

<210> SEQ ID NO 7
<211> LENGTH: 75
<212> TYPE: DNA
<213> ORGANISM: Artificial Sequence
<220> FEATURE:
<223> OTHER INFORMATION: dna for spacer peptide

<400> SEQUENCE: 7
gtgcccctgt ctgatgctga cttgcagact ttggcaagtc agattcagca aatcaacgat        60
acttctgatt ctgca                                                         75

<210> SEQ ID NO 8
<211> LENGTH: 75
<212> TYPE: DNA
<213> ORGANISM: Artificial Sequence
<220> FEATURE:
<223> OTHER INFORMATION: dna for spacer peptide

<400> SEQUENCE: 8
gcaggtgtgg attacctgcc taccatcggc caagtgccga catacaccaa gttccagccc        60
acagccgatc cgggc                                                         75

<210> SEQ ID NO 9
<211> LENGTH: 49
<212> TYPE: PRT
<213> ORGANISM: Artificial Sequence
<220> FEATURE:
<223> OTHER INFORMATION: secretion signal peptide (SP56) with spacer

<400> SEQUENCE: 9

Met Lys Lys Lys Lys Thr Ile Ser Ala Ala Leu Ala Thr Ala Leu Ala
1               5                   10                  15

Leu Thr Cys Met Gly Ser Gly Gly Gly Thr Ala Phe Ala Val Pro Leu
            20                  25                  30

Ser Asp Ala Asp Leu Gln Thr Leu Ala Ser Gln Ile Gln Gln Ile Asn
        35                  40                  45

Asp

<210> SEQ ID NO 10
<211> LENGTH: 53
<212> TYPE: PRT
<213> ORGANISM: Artificial Sequence
<220> FEATURE:
<223> OTHER INFORMATION: secretion signal peptide (SP67) with spacer

<400> SEQUENCE: 10

```
Met Lys Ile Asn Asn Lys Gly Lys Gly Ala Leu Ile Ala Ala Ile Thr
1               5                   10                  15
Ala Ala Ala Thr Leu Leu Ser Cys Gly Leu Ala Ala Ala Ser Ala Ser
            20                  25                  30
Ala Ala Gly Val Asp Tyr Leu Pro Thr Ile Gly Gln Val Pro Thr Tyr
        35                  40                  45
Thr Lys Phe Gln Pro
    50
```

<210> SEQ ID NO 11
<211> LENGTH: 147
<212> TYPE: DNA
<213> ORGANISM: Artificial Sequence
<220> FEATURE:
<223> OTHER INFORMATION: dna for secretion signal peptide (SP56) with spacer

<400> SEQUENCE: 11

```
atgaaaaaga agaagactat atcggctgcg ctggcaacag cgttagcctt aacctgcatg     60
ggcagcgggg gaggtactgc gttcgcagtg cccctgtctg atgctgactt gcagactttg    120
gcaagtcaga ttcagcaaat caacgat                                        147
```

<210> SEQ ID NO 12
<211> LENGTH: 159
<212> TYPE: DNA
<213> ORGANISM: Artificial Sequence
<220> FEATURE:
<223> OTHER INFORMATION: dna for secretion signal peptide (SP67) with spacer

<400> SEQUENCE: 12

```
atgaagataa acaataaggg caagggcgct cttatcgcgg caattaccgc cgcggcaacg     60
ctattgtcat gcgggctggc cgctgcaagt gccagtgcgg caggtgtgga ttacctgcct    120
accatcggcc aagtgccgac atacaccaag ttccagccc                           159
```

<210> SEQ ID NO 13
<211> LENGTH: 361
<212> TYPE: DNA
<213> ORGANISM: Artificial Sequence
<220> FEATURE:
<223> OTHER INFORMATION: Hu promoter

<400> SEQUENCE: 13

```
gtcttcctgc tggcctatgc attgggttcc gcagtgccca ctccaggcgg tctgggcggt     60
gtggaagcgg cgctgacatt cgcgttcgtg gcggtcggag tgccgcaggg cgtggcgctt    120
tccgccactt tgctgcaccg cgtggtgttc tactggctgc gcattccgct gggcgcggcg    180
gccatgaagt ggcttgacaa gcataatctt gtctgattcg tctatttca taccccttc      240
ggggaaatag atgtgaaaac ccttataaaa cgcgggtttt cgcagaaaca tgcgctagta    300
tcattgatga caacatggac taagcaaaag tgcttgtccc ctgacccaag aaggatgctt    360
t                                                                    361
```

<210> SEQ ID NO 14
<211> LENGTH: 3780
<212> TYPE: DNA
<213> ORGANISM: Artificial Sequence
<220> FEATURE:
<223> OTHER INFORMATION: sequence of pFGF110

<400> SEQUENCE: 14

```
agatccgtct tcctgctggc ctatgcattg ggttccgcag tgcccactcc aggcggtctg      60
ggcggtgtgg aagcggcgct gacattcgcg ttcgtggcgg tcggagtgcc gcagggcgtg     120
gcgctttccg ccactttgct gcaccgcgtg gtgttctact ggctgcgcat tccgctgggc     180
gcggcggcca tgaagtggct tgacaagcat aatcttgtct gattcgtcta ttttcatacc     240
cccttcgggg aaatagatgt gaaaacccct ataaaacgcg gttttcgca  gaaacatgcg     300
ctagtatcat tgatgacaac atggactaag caaaagtgct tgtcccctga cccaagaagg     360
atgctttatg aaaaagaaga agactatatc ggctgcgctg gcaacagcgt tagccttaac     420
ctgcatgggc agcgggggag gtactgcgtt cgcagtgccc ctgtctgatg ctgacttgca     480
gactttggca agtcagattc agcaaatcaa cgatgccgcc ggctcgatca ccaccctgcc     540
ggccctgccg gaggatggcg gctcgggcgc cttcccgccg ggccacttca aggacccgaa     600
gcgcctgtac tgcaagaacg gcggcttctt cctgcgtatc caccggacg gccgtgtgga      660
tggcgtccgt gagaagagcg acccgcatat caagctgcag ctgcaggccg aggaacgtgg     720
cgtggtctcc atcaagggcg tgtgcgccaa ccgctacctg gccatgaagg aagacggccg     780
tctgctggcc tcgaagtgcg tcaccgatga atgcttcttc ttcgagcgcc tggaatccaa     840
caactacaac acctaccgct cccgtaagta caccagctgg tacgtggccc tgaagcgtac     900
cggccagtac aagctgggca gcaagaccgg cccgggccag aaggccatcc tgttcctgcc     960
gatgtccgcc aagtcgtgac cttctgctcg tagcgattac ttcgagcatt actgacgaca    1020
aagaccccga ccgagatggt cggggtcttt ttgttgtggt gctgtgacgt gttgtccaac    1080
cgtattattc cggactagtc ctccaggacc tcgtctacga ggcgctgagc gaggaatggc    1140
gcaaaaggga cggcgagatc agcgacccat gggccaacga cgaggcggac ggataccagc    1200
cgccctcata cgagccggtc aaccccgaac gcaggactcc ccagacgccc tccgatggcc    1260
tgatctgacg tccgaaaaaa ggcgctgtgc gccctttta  aatctttat  aaatctttt     1320
acattctttt agcccctccg cagccttact ctcccaacgg gtttcagccg aaacctacac    1380
caaaagggga gcgaacctac accaaaaggg gagcgaacct acaccaaaag gggagcgaac    1440
ctacaccaaa aggggagcta tatacaccctt ttgttattta aggtgcaagt tgtgctatgc    1500
tgaggccatg tccaatgaga tcgtgaagtt cagcaaccag ttcaacaacg tcgcgctgaa    1560
gaagttcgac gccgtgcacc tggacgtgct catggcgatc gcctcaaggg tgagggagaa    1620
gggcacggcc acgtggagt  tctcgttcga ggagctgcgc ggcctcatgc gattgaggaa    1680
gaacctgacc aacaagcagc tggccgacaa gatcgtgcag acgaacgcgc gcctgctggc    1740
gctgaactac atgttcgagg attcgggcaa gatcatccag ttcgcgctgt tcacgaagtt    1800
cgtcaccgac ccgcaggagg cgactctcgc ggttggggtc aacgaggagt tcgcgttcct    1860
gctcaacgac ctgaccagcc agttcacgcg cttcgagctg gccgagttcg ccgacctcaa    1920
gagcaagtac gccaaggagt ctaccgcag gggcaagcag taccgcagct ccggaatctg    1980
gaagatcggc cgcgacgagt tctgccgact gcttggcgtt ccaccgtcgg caataaccca    2040
gacacgatat ctgaatcaga aggttcttca gccaattcag gaggagtgtg gcctctcct    2100
```

```
tggcctgaag atcgagcgcc agtacgtgaa acgcaggctg tcgggcttcg tgttcacatt    2160
cgcccgcgag acccctccgg tgatcgacgc caggcccgtg gaggcgagga agacggacgg    2220
cgacggcaag ggccattgga cgagcgttgc cgggtacggc gaggtgttca cgaccacggc    2280
gttgttcgac gtgacggccg cccgggctca cttcgacggc accgttgaag ccggggagtg    2340
ccgtttctgc gcgtttgacg cgcgcaaccg cgaacatcat gcgcggaacg ccggaaggct    2400
gttctagcgg ccgtgtccgc gcctctgggg cggttgcgcc tgccatgggt cgatctgccg    2460
ctgttcggcc tcacgctggt ctgtgcgctg cctgatctcc ctgagcaggt cggccttggt    2520
cctgggggcg cttcgctcct cgaacgggcc gctctccccc aggtcctcgg gctcgctcag    2580
gtccaacggc tcgtcaccgg acggctcggg ccggttctct ccctgtgccg ggttctccgc    2640
ctgtgcgcgt tgttcggcca tcgcagtgc gagggcctc acctgttcgg ggcttgtcga    2700
ctcgattttc gttcgtgaat acatgttata ataactataa ctaataacgt aacgtgactg    2760
gcaagagata ttttaaaaac aatgaatagg tttacactta ctttagtttt atggaaatga    2820
aagatcatat catatataat ctagaataaa attaactaaa ataattatta tctagataaa    2880
aaatttagaa gccaatgaaa tctataaata aactaaatta gtttattta attacaact    2940 atggatataa ataggtact aatcaaata gtgaggagga tatatttgaa tacatacgaa    3000
caaattaata aagtgaaaa aatacttcgg aaacatttaa aaaataacct tattggtact    3060
tacatgtttg gatcaggagt tgagagtgga ctaaaccaa atagtgatct tgacttttta    3120
gtcgtcgtat ctgaaccatt gacagatcaa agtaaagaaa tacttataca aaaaattaga    3180 cctattcaa aaaaatagg agataaaaagc aacttacgat atattgaatt aacaattatt    3240
attcagcaag aaatggtacc gtggaatcat cctcccaaac aagaatttat ttatggagaa    3300
tggttacaag agctttatga acaaggatac attcctcaga aggaattaaa ttcagattta    3360
accataatgc tttaccaagc aaaacgaaaa aataaaagaa tatacggaaa ttatgactta    3420
gaggaattac tacctgatat tccattttct gatgtgagaa gagccattat ggattcgtca    3480
gaggaattaa tagataatta tcaggatgat gaaaccaact ctatattaac tttatgccgt    3540 atgatttaa ctatggacac gggtaaaatc ataccaaaag atattgcggg aaatgcagtg    3600
gctgaatctt ctccattaga acataggggag agaattttgt tagcagttcg tagttatctt    3660
ggagagaata ttgaatggac taatgaaaat gtaaatttaa ctataaacta tttaaataac    3720 agattaaaaaa aattataaaa aaattgaaaa aatggtggaa acactttttt caatttttt    3780
```

<210> SEQ ID NO 15
<211> LENGTH: 3792
<212> TYPE: DNA
<213> ORGANISM: Artificial Sequence
<220> FEATURE:
<223> OTHER INFORMATION: sequence of pFGF111

<400> SEQUENCE: 15

```
agatccgtct tcctgctggc ctatgcattg ggttccgcag tgcccactcc aggcggtctg     60
ggcggtgtgg aagcggcgct gacattcgcg ttcgtggcgg tcggagtgcc gcagggcgtg    120
gcgctttccg ccactttgct gcaccgcgtg gtgttctact ggctgcgcat tccgctgggc    180
gcggcggcca tgaagtggct tgacaagcat aatcttgtct gattcgtcta ttttcatacc    240
cccttcgggg aaatagatgt gaaaacccctt ataaaacgcg gttttcgca gaaacatgcg    300 ctagtatcat tgatgacaac atggactaag caaaagtgct tgtcccctga cccaagaagg    360
atgctttatg aagataaaca ataagggcaa gggcgctctt atcgcggcaa ttaccgccgc    420
```

```
ggcaacgcta ttgtcatgcg ggctggccgc tgcaagtgcc agtgcggcag gtgtggatta    480
cctgcctacc atcggccaag tgccgacata caccaagttc cagcccgccg ccggctcgat    540
caccaccctg ccggccctgc cggaggatgg cggctcgggc gccttcccgc cgggccactt    600
caaggacccg aagcgcctgt actgcaagaa cggcggcttc ttcctgcgta tccacccgga    660
cggccgtgtg gatggcgtcc gtgagaagag cgacccgcat atcaagctgc agctgcaggc    720
cgaggaacgt ggcgtggtct ccatcaaggg cgtgtgcgcc aaccgctacc tggccatgaa    780
ggaagacggc cgtctgctgg cctcgaagtg cgtcaccgat gaatgcttct tcttcgagcg    840
cctggaatcc aacaactaca cacctaccg ctcccgtaag tacaccagct ggtacgtggc    900
cctgaagcgt accggccagt acaagctggg cagcaagacc ggcccgggcc agaaggccat    960
cctgttcctg ccgatgtccg ccaagtcgtg accttctgct cgtagcgatt acttcgagca   1020
ttactgacga caaagacccc gaccgagatg gtcgggtct ttttgttgtg gtgctgtgac   1080
gtgttgtcca accgtattat tccggactag tcctccagga cctcgtctac gaggcgctga   1140
gcgaggaatg gcgcaaaagg gacggcgaga tcagcgaccc atgggccaac gacgaggcgg   1200
acggatacca gccgccctca tacgagccgt caaccccga acgcaggact ccccagacgc   1260
cctccgatgg cctgatctga cgtccgaaaa aaggcgctgt gcgccctttt taaatctttt   1320
ataaatcttt ttacattctt ttagcccctc cgcagcctta ctctcccaac gggtttcagc   1380
cgaaacctac accaaagggg agcgaacct acaccaaaag gggagcgaac ctacaccaaa   1440
aggggagcga acctacacca aaagggagc tatatacacc tttgttatt taaggtgcaa   1500
gttgtgctat gctgaggcca tgtccaatga gatcgtgaag ttcagcaacc agttcaacaa   1560
cgtcgcgctg aagaagttcg acgccgtgca cctggacgtg ctcatggcga tcgcctcaag   1620
ggtgagggag aagggcacgg ccacggtgga gttctcgttc gaggagctgc gcggcctcat   1680
gcgattgagg aagaacctga ccaacaagca gctggccgac aagatcgtgc agacgaacgc   1740
gcgcctgctg cgcgctgaact acatgttcga ggattcgggc aagatcatcc agttcgcgct   1800
gttcacgaag ttcgtcaccg acccgcagga ggcgactctc gcggttgggg tcaacgagga   1860
gttcgcgttc ctgctcaacg acctgaccag ccagttcacg cgcttcgagc tggccgagtt   1920
cgccgacctc aagagcaagt acgccaagga gttctaccgc agggccaagc agtaccgcag   1980
ctccggaatc tggaagatcg gccgcgacga gttctgccga ctgcttggcg ttccaccgtc   2040
ggcaataacc cagacacgat atctgaatca gaaggttctt cagccaattc aggaggagtg   2100
tgggcctctc cttggcctga agatcgagcg ccagtacgtg aaacgcaggc tgtcgggctt   2160
cgtgttcaca ttcgcccgcg agacccctcc ggtgatcgac gccaggcccg tggaggcgag   2220
gaagacggac ggcgacggca agggccattg gacgagcgtt gccgggtacg cgcaggtgtt   2280
cacgaccacg gcgttgttcg acgtgacggc cgcccgggct cacttcgacg gcaccgttga   2340
agccggggag tgccgtttct gcgcgtttga cgcgcgcaac cgcgaacatc atgcgcggaa   2400
cgccggaagg ctgttctagc ggccgtgtcc gcgcctctgg ggcggttgcg cctgccatgg   2460
gtcgatctgc cgctgttcgg cctcacgctg gtctgtgcgc tgcctgatct ccctgagcag   2520
gtcggccttg gtcctggggg cgcttcgctc tcgaacggg ccgctctccc ccaggtcctc   2580
gggctcgctc aggtccaacg gctcgtcacc ggacggctcg ggccggttct ctccctgtgc   2640
cgggttctcc gcctgtgcgc gttgttcggc catgcgcagt gcgagggcct tcacctgttc   2700
ggggcttgtc gactcgattt tcgttcgtga atacatgtta taataactat aactaataac   2760
gtaacgtgac tggcaagaga tatttttaaa acaatgaata ggtttacact tactttagtt   2820
```

```
ttatggaaat gaaagatcat atcatatata atctagaata aaattaacta aaataattat    2880
tatctagata aaaaatttag aagccaatga aatctataaa taaactaaat taagttttatt   2940 taattaacaa ctatggatat aaaataggta ctaatcaaaa tagtgaggag gatatatttg    3000
aatacatacg aacaaattaa taaagtgaaa aaaatacttc ggaaacattt aaaaaataac    3060
cttattggta cttacatgtt tggatcagga gttgagagtg gactaaaacc aaatagtgat    3120
cttgactttt tagtcgtcgt atctgaacca ttgacagatc aaagtaaaga aatacttata    3180
caaaaaatta gacctatttc aaaaaaaata ggagataaaa gcaacttacg atatattgaa    3240
ttaacaatta ttattcagca agaaatggta ccgtggaatc atcctcccaa acaagaattt    3300
atttatggag aatggttaca agagctttat gaacaaggat acattcctca gaaggaatta    3360
aattcagatt taaccataat gctttaccaa gcaaaacgaa aaaataaaag aatatacgga    3420
aattatgact tagaggaatt actacctgat attccatttt ctgatgtgag aagagccatt    3480
atggattcgt cagaggaatt aatagataat tatcaggatg atgaaaccaa ctctatatta    3540
actttatgcc gtatgatttt aactatggac acgggtaaaa tcataccaaa agatattgcg    3600
ggaaatgcag tggctgaatc ttctccatta gaacataggg agagaatttt gttagcagtt    3660
cgtagttatc ttggagagaa tattgaatgg actaatgaaa atgtaaattt aactataaac    3720
tatttaaata acagattaaa aaaattataa aaaaattgaa aaaatggtgg aaacactttt    3780
ttcaattttt tt                                                         3792

<210> SEQ ID NO 16
<211> LENGTH: 262
<212> TYPE: DNA
<213> ORGANISM: Bifidobacterium longum

<400> SEQUENCE: 16
ctcccaaact tgcagagcc cgaccatcgt ggtcgggctt tttgtgttgt ccgggtggat      60
ttgcataata ggaaagcttg tgtctggaga ggagactcgc tagcacagca cagcaatata    120
agttgcggga ggagaccgac cacaggccga ttgcctacag catgcacgga taaataatga    180
gtcaagaccg agcatgatgg cagacagccg aacctgagga cggcgaccat tcgaaccgcg    240
ttatagaaag aagaaccata at                                              262

<210> SEQ ID NO 17
<211> LENGTH: 44
<212> TYPE: DNA
<213> ORGANISM: Artificial Sequence
<220> FEATURE:
<223> OTHER INFORMATION: SP56 ins F1 primer

<400> SEQUENCE: 17
caagaaggat gctttatgaa aagaagaag actatatcgg ctgc                       44

<210> SEQ ID NO 18
<211> LENGTH: 41
<212> TYPE: DNA
<213> ORGANISM: Artificial Sequence
<220> FEATURE:
<223> OTHER INFORMATION: SP56 ins R1 FGF primer

<400> SEQUENCE: 18
gatcgagccg gcggcatcgt tgatttgctg aatctgactt g                         41
```

<210> SEQ ID NO 19
<211> LENGTH: 40
<212> TYPE: DNA
<213> ORGANISM: Artificial Sequence
<220> FEATURE:
<223> OTHER INFORMATION: SP67 ins F1 primer

<400> SEQUENCE: 19
caagaaggat gctttatgaa gataaacaat aagggcaagg                40

<210> SEQ ID NO 20
<211> LENGTH: 37
<212> TYPE: DNA
<213> ORGANISM: Artificial Sequence
<220> FEATURE:
<223> OTHER INFORMATION: SP67 ins R1 FGF primer

<400> SEQUENCE: 20
gatcgagccg gcggcgggct ggaacttggt gtatgtc                   37

<210> SEQ ID NO 21
<211> LENGTH: 29
<212> TYPE: DNA
<213> ORGANISM: Artificial Sequence
<220> FEATURE:
<223> OTHER INFORMATION: FGF1 primer

<400> SEQUENCE: 21
accatcatca ttgaccttct gctcgtagc                            29

<210> SEQ ID NO 22
<211> LENGTH: 31
<212> TYPE: DNA
<213> ORGANISM: Artificial Sequence
<220> FEATURE:
<223> OTHER INFORMATION: FGF2 primer

<400> SEQUENCE: 22
cgagccggcg gccataaagc atccttcttg g                         31

<210> SEQ ID NO 23
<211> LENGTH: 43
<212> TYPE: DNA
<213> ORGANISM: Artificial Sequence
<220> FEATURE:
<223> OTHER INFORMATION: FGF3 primer

<400> SEQUENCE: 23
gtcaatgatg atggtggtgg tgcgacttgg cggacatcgg cag            43

<210> SEQ ID NO 24
<211> LENGTH: 20
<212> TYPE: DNA
<213> ORGANISM: Artificial Sequence
<220> FEATURE:
<223> OTHER INFORMATION: FGF4 primer

<400> SEQUENCE: 24
atggccgccg gctcgatcac                                      20

<210> SEQ ID NO 25
<211> LENGTH: 24
<212> TYPE: DNA
<213> ORGANISM: Artificial Sequence
<220> FEATURE:
<223> OTHER INFORMATION: FGF35 primer

```
<400> SEQUENCE: 25
gccgccggct cgatcaccac cctg                                           24

<210> SEQ ID NO 26
<211> LENGTH: 19
<212> TYPE: DNA
<213> ORGANISM: Artificial Sequence
<220> FEATURE:
<223> OTHER INFORMATION: Hu Prom R primer

<400> SEQUENCE: 26
aaagcatcct tcttgggtc                                                 19

<210> SEQ ID NO 27
<211> LENGTH: 36
<212> TYPE: DNA
<213> ORGANISM: Artificial Sequence
<220> FEATURE:
<223> OTHER INFORMATION: Hu SP26 F primer

<400> SEQUENCE: 27
caagaaggat gctttatgaa gaagaaagct cttgct                              36

<210> SEQ ID NO 28
<211> LENGTH: 36
<212> TYPE: DNA
<213> ORGANISM: Artificial Sequence
<220> FEATURE:
<223> OTHER INFORMATION: FGF SP26L20 R primer

<400> SEQUENCE: 28
gatcgagccg gcggcgttct gcggttcgga gttgta                              36

<210> SEQ ID NO 29
<211> LENGTH: 33
<212> TYPE: DNA
<213> ORGANISM: Artificial Sequence
<220> FEATURE:
<223> OTHER INFORMATION: FGF His F primer

<400> SEQUENCE: 29
tgaccttctg ctcgtagcga ttacttcgag cat                                 33

<210> SEQ ID NO 30
<211> LENGTH: 36
<212> TYPE: DNA
<213> ORGANISM: Artificial Sequence
<220> FEATURE:
<223> OTHER INFORMATION: FGF His R primer

<400> SEQUENCE: 30
acgagcagaa ggtcacgact tggcggacat cggcag                              36

<210> SEQ ID NO 31
<211> LENGTH: 486
<212> TYPE: DNA
<213> ORGANISM: Artificial Sequence
<220> FEATURE:
<223> OTHER INFORMATION: FGF2-His sequence

<400> SEQUENCE: 31
atggccgccg gctcgatcac caccctgccg gccctgccgg aggatggcgg ctcgggcgcc    60
ttcccgccgg gccactttaa ggacccgaag cgcctgtact gcaagaacgg cggcttcttc   120
ctgcgtatcc acccggacgg ccgtgtggat ggcgtccgtg agaagagcga cccgcatatc   180
```

| | |
|---|---|
| aagctgcagc tgcaggccga ggaacgtggc gtggtctcca tcaagggcgt gtgcgccaac | 240 |
| cgctacctgg ccatgaagga agacggccgt ctgctggcct cgaagtgcgt caccgatgaa | 300 |
| tgcttcttct tcgagcgcct ggaatccaac aactacaaca cctaccgctc ccgtaagtac | 360 |
| accagctggt acgtggccct gaagcgtacc ggccagtaca agctgggcag caagaccggc | 420 |
| ccgggccaga aggccatcct gttcctgccg atgtccgcca agtcgcacca ccaccatcat | 480 |
| cattga | 486 |

```
<210> SEQ ID NO 32
<211> LENGTH: 5150
<212> TYPE: DNA
<213> ORGANISM: Artificial Sequence
<220> FEATURE:
<223> OTHER INFORMATION: pCDshuttle dna

<400> SEQUENCE: 32
```

| | |
|---|---|
| ggatccgtct tcctgctggc ctatgcattg ggttccgcag tgcccactcc aggcggtctg | 60 |
| ggcggtgtgg aagcggcgct gacattcgcg ttcgtggcgg tcggagtgcc gcagggcgtg | 120 |
| gcgctttccg ccactttgct gcaccgcgtg gtgttctact ggctgcgcat tccgctgggc | 180 |
| gcggcggcca tgaagtggct tgacaagcat aatcttgtct gattcgtcta ttttcatacc | 240 |
| cccttcgggg aaatagatgt gaaaacccct ataaaacgcg gttttcgca gaaacatgcg | 300 |
| ctagtatcat tgatgacaac atggactaag caaaagtgct tgtcccctga cccaagaagg | 360 |
| atgctttatg gcatacaaca agtctgacct cgtttcgaat aacgctttac aaacaattat | 420 |
| taacgcccgg ttaccaggcg aagaggggct gtggcagatt catctgcagg acggaaaaat | 480 |
| cagcgccatt gatgcgcaat ccggcgtgat gcccataact gaaaacagcc tggatgccga | 540 |
| acaaggttta gttataccgc cgtttgtgga gccacatatt caccaggaca ccacgcaaac | 600 |
| cgccggacaa ccgaactgga atcagtccgg cacgctgttt gaaggcattg aacgctgggc | 660 |
| cgagcgcaaa gcgttattaa cccatgacga tgtgaaacaa cgcgcatggc aaacgctgaa | 720 |
| atggcagatt gccaacggca ttcagcatgt gcgtacccat gtcgatgttt cggatgcaac | 780 |
| gctaactgcg ctgaaagcaa tgctggaagt gaagcaggaa gtcgcgccgt ggattgatct | 840 |
| gcaaatcgtc gccttccctc aggaagggat tttgtcgtat cccaacggtg aagcgttgct | 900 |
| ggaagaggcg ttacgcttag ggcagatgt agtgggggcg attccgcatt ttgaatttac | 960 |
| ccgtgaatac ggcgtggagt cgctgcataa aaccttcgcc ctggcgcaaa aatacgaccg | 1020 |
| tctcatcgac gttcactgtg atgagatcga tgacgagcag tcgcgctttg tcgaaaccgt | 1080 |
| tgctgccctg gcgcaccatg aaggcatggg cgcgcgagtc accgccagcc acaccacggc | 1140 |
| aatgcactcc tataacgggg cgtataccgc acgcctgttc cgcttgctga aaatgtccgg | 1200 |
| tattaacttt gtcgccaacc cgctggtcaa tattcatctg caaggacgtt cgatacgta | 1260 |
| tccaaaacgt cgcggcatca cgcgcgttaa agagatgctg gagtccggca ttaacgtctg | 1320 |
| ctttggtcac gatgctgtct tcgatccgtg gtatccgctg ggaacggcga atatgctgca | 1380 |
| agtgctgcat atggggctgc atgtttgcca gttgatgggc tacgggcaga ttaacgatgg | 1440 |
| cctgaattta atcacccacc acagcgcaag gacgttgaat ttgcaggatt acggcattgc | 1500 |
| cgccggaaac agcgccaacc tgattatcct gccggctgaa aatgggtttg atgcgctgcg | 1560 |
| ccgtcaggtt ccggtacgtt attcggtacg tggcggcaag gtgattgcca gcacacaacc | 1620 |
| ggcacaaacc accgtatatc tggagcagcc agaagccatc gattacaaac gttgaccttc | 1680 |
| tgctcgtagc gattacttcg agcattactg acgacaaaga ccccgaccga gatggtcggg | 1740 |

-continued

```
gtcttttgt tgtggtgctg tgacgtgttg tccaaccgta ttattccgga ctagtcctcc       1800
aggacctcgt ctacgaggcg ctgagcgagg aatggcgcaa aagggacggc gagatcagcg       1860
acccatgggc caacgacgag gcggacggat accagccgcc ctcatacgag ccggtcaacc       1920
ccgaacgcag gactcccag acgccctccg atggcctgat ctgacgtccg aaaaaaggcg       1980
ctgtgcgccc tttttaaatc ttttataaat cttttttacat tcttttagcc cctccgcagc    2040
cttactctcc caacgggttt cagccgaaac ctacaccaaa aggggagcga acctacacca     2100
aaggggagc gaacctacac caaaagggga gcgaacctac accaaaaggg gagctatata     2160
caccttttgt tatttaaggt gcaagttgtg ctatgctgag gccatgtcca atgagatcgt    2220
gaagttcagc aaccagttca acaacgtcgc gctgaagaag ttcgacgccg tgcacctgga    2280
cgtgctcatg gcgatcgcct caaggtgag ggagaagggc acggccacgg tggagttctc    2340
gttcgaggag ctgcgcggcc tcatgcgatt gaggaagaac ctgaccaaca gcagctggc    2400
cgacaagatc gtgcagacga acgcgcgcct gctggcgctg aactacatgt tcgaggattc    2460
gggcaagatc atccagttcg cgctgttcac gaagttcgtc accgacccgc aggaggcgac    2520
tctcgcggtt ggggtcaacg aggagttcgc gttcctgctc aacgacctga ccagccagtt    2580
cacgcgcttc gagctggccg agttcgccga cctcaagagc aagtacgcca aggagttcta    2640
ccgcagggcc aagcagtacc gcagctccgg aatctggaag atcggccgcg acgagttctg    2700
ccgactgctt ggcgttccac cgtcggcaat aacccagaca cgatatctga atcagaaggt    2760
tcttcagcca attcaggagg agtgtgggcc tctccttggc ctgaagatcg agcgccagta    2820
cgtgaaacgc aggctgtcgg gcttcgtgtt cacattcgcc cgcgagaccc ctccggtgat    2880
cgacgccagg cccgtggagg cgaggaagac ggacggcgac ggcaagggcc attggacgag    2940
cgttgccggg tacggcgagg tgttcacgac cacggcgttg ttcgacgtga cggccgcccg    3000
ggctcacttc gacggcaccg ttgaagccgg gggagtgccgt ttctgcgcgt ttgacgcgcg    3060
caaccgcgaa catcatgcgc ggaacgccgg aaggctgttc tagcggccgt gtccgcgcct    3120
ctggggcggt tgcgcctgcc atgggtcgat ctgccgctgt tcggcctcac gctggtctgt    3180
gcgctgcctg atctccctga gcaggtcggc cttggtcctg ggggcgcttc gctcctcgaa    3240
cgggccgctc tcccccaggt cctcgggctc gctcaggtcc aacggctcgt caccggacgg    3300
ctcgggccgg ttctctcccct gtgccgggtt tccgcctgt gcgcgttgtt cggccatgcg    3360
cagtgcgagg gccttcacct gttcggggct tgtcgactcg attttcgttc gtgaatacat    3420
gttataataa ctataactaa taacgtaacg tgactggcaa gagatatttt taaaacaatg    3480
aataggttta cacttacttt agttttatgg aaatgaaaga tcatatcata tataatctag    3540
aataaaatta actaaaataa ttattatcta gataaaaaat ttagaagcca atgaaatcta    3600
taaataaact aaattaagtt tatttaatta acaactatgg atataaaata ggtactaatc    3660
aaaatagtga ggaggatata tttgaataca tacgaacaaa ttaataaagt gaaaaaaata    3720
cttcggaaac atttaaaaaa taaccttatt ggtacttaca tgtttggatc aggagttgag    3780
agtggactaa aaccaaatag tgatcttgac tttttagtcg tcgtatctga accattgaca    3840
gatcaaagta agaaatact tatacaaaaa attagaccta tttcaaaaaa aataggagat    3900
aaaagcaact tacgatatat tgaattaaca attattattc agcaagaaat ggtaccgtgg    3960
aatcatcctc ccaaacaaga atttatttat ggagaatggt tacaagagct ttatgaacaa    4020
ggatacattc tcagaagga attaaattca gatttaacca taatgcttta ccaagcaaaa    4080
cgaaaaaata aaagaatata cggaaattat gacttagagg aattactacc tgatattcca    4140
```

```
ttttctgatg tgagaagagc cattatggat tcgtcagagg aattaataga taattatcag   4200
gatgatgaaa ccaactctat attaacttta tgccgtatga ttttaactat ggacacgggt   4260
aaaatcatac caaaagatat tgcgggaaat gcagtggctg aatcttctcc attagaacat   4320
agggagagaa ttttgttagc agttcgtagt tatcttggag agaatattga atggactaat   4380
gaaaatgtaa atttaactat aaactatttta aataacagat taaaaaaatt ataaaaaaat   4440
tgaaaaaatg gtggaaacac ttttttcaat tttttttagat cttgagcaaa aggccagcaa   4500
aaggccagga accgtaaaaa ggccgcgttg ctggcgtttt tccataggct ccgcccccct   4560
gacgagcatc acaaaaatcg acgctcaagt cagaggtggc gaaacccgac aggactataa   4620
agataccagg cgtttccccc tggaagctcc ctcgtgcgct ctcctgttcc gaccctgccg   4680
cttaccggat acctgtccgc ctttctccct tcgggaagcg tggcgctttc tcatagctca   4740
cgctgtaggt atctcagttc ggtgtaggtc gttcgctcca agctgggctg tgtgcacgaa   4800
ccccccgttc agcccgaccg ctgcgcctta tccggtaact atcgtcttga gtccaacccg   4860
gtaagacacg acttatcgcc actggcagca gccactggta acaggattag cagagcgagg   4920
tatgtaggcg gtgctacaga gttcttgaag tggtggccta actacggcta cactagaaga   4980
acagtatttg gtatctgcgc tctgctgaag ccagttacct tcggaaaaag agttggtagc   5040
tcttgatccg gcaaacaaac caccgctggt agcggtggtt ttttttgtttg caagcagcag   5100
attacgcgca gaaaaaaagg atctcaagaa gatcctttga tcttttctac              5150
```

```
<210> SEQ ID NO 33
<211> LENGTH: 4325
<212> TYPE: DNA
<213> ORGANISM: Artificial Sequence
<220> FEATURE:
<223> OTHER INFORMATION: linear fragment of pHu-FGF2

<400> SEQUENCE: 33
```

```
gccgccggct cgatcaccac cctgccggcc ctgccggagg atggcggctc gggcgccttc     60
ccgccgggcc acttcaagga cccgaagcgc ctgtactgca agaacggcgg cttcttcctg    120
cgtatccacc cggacggccg tgtggatggc gtccgtgaga gagcgaccc gcatatcaag    180
ctgcagctgc aggccgagga acgtggcgtg gtctccatca agggcgtgtg cgccaaccgc    240
tacctggcca tgaaggaaga cggccgtctg ctggcctcga agtgcgtcac cgatgaatgc    300
ttcttcttcg agcgcctgga atccaacaac tacaacacct accgctcccg taagtacacc    360
agctggtacg tggcccctgaa gcgtaccggc cagtacaagc tgggcagcaa gaccggcccg    420
ggccagaagg ccatcctgtt cctgccgatg tccgccaagt cgcaccacca ccatcatcat    480
tgaccttctg ctcgtagcga ttacttcgag cattactgac gacaaagacc ccgaccgaga    540
tggtcggggt cttttttgttg tggtgctgtg acgtgttgtc caaccgtatt attccggact    600
agtcctccag gacctcgtct acgaggcgct gagcgaggaa tggcgcaaaa gggacggcga    660
gatcagcgac ccatgggcca acgacgaggc ggacggatac cagccgccct catacgagcc    720
ggtcaacccc gaacgcagga ctccccagac gccctccgat ggcctgatct gacgtccgaa    780
aaaaggcgct gtgcgccctt tttaaatctt ttataaatct ttttacattc ttttttagccc    840
tccgcagcct tactctccca acgggtttca gccgaaacct acaccaaaag gggagcgaac    900
ctacaccaaa aggggagcga acctacacca aaaggggagc gaacctacac caaaagggga    960
gctatataca ccttttgtta tttaaggtgc aagttgtgct atgctgaggc catgtccaat   1020
gagatcgtga agttcagcaa ccagttcaac aacgtcgcgc tgaagaagtt cgacgccgtg   1080
```

-continued

```
cacctggacg tgctcatggc gatcgcctca agggtgaggg agaagggcac ggccacggtg   1140
gagttctcgt tcgaggagct gcgcggcctc atgcgattga ggaagaacct gaccaacaag   1200
cagctggccg acaagatcgt gcagacgaac gcgcgcctgc tggcgctgaa ctacatgttc   1260
gaggattcgg gcaagatcat ccagttcgcg ctgttcacga agttcgtcac cgacccgcag   1320
gaggcgactc tcgcggttgg ggtcaacgag gagttcgcgt tcctgctcaa cgacctgacc   1380
agccagttca cgcgcttcga gctggccgag ttcgccgacc tcaagagcaa gtacgccaag   1440
gagttctacc gcagggccaa gcagtaccgc agctccggaa tctggaagat cggccgcgac   1500
gagttctgcc gactgcttgg cgttccaccg tcggcaataa cccagacacg atatctgaat   1560
cagaaggttc ttcagccaat tcaggaggag tgtgggcctc tccttggcct gaagatcgag   1620
cgccagtacg tgaaacgcag gctgtcgggc ttcgtgttca cattcgcccg cgagacccct   1680
ccggtgatcg acgccaggcc cgtggaggcg aggaagacgg acggcgacgg caagggccat   1740
tggacgagcg ttgccgggta cggcgaggtg ttcacgacca cggcgttgtt cgacgtgacg   1800
gccgcccggg ctcacttcga cggcaccgtt gaagccgggg agtgccgttt ctgcgcgttt   1860
gacgcgcgca accgcgaaca tcatgcgcgc aacgccggaa ggctgttcta gcggccgtgt   1920
ccgcgcctct ggggcggttg cgcctgccat gggtcgatct gccgctgttc ggcctcacgc   1980
tggtctgtgc gctgcctgat ctccctgagc aggtcggcct tggtcctggg ggcgcttcgc   2040
tcctcgaacg ggccgctctc ccccaggtcc tcgggctcgc tcaggtccaa cggctcgtca   2100
ccggacggct cgggccggtt ctctcccctgt gccgggttct ccgcctgtgc gcgttgttcg   2160
gccatgcgca gtgcgagggc cttcacctgt cggggcttg tcgactcgat tttcgttcgt   2220
gaatacatgt tataataact ataactaata acgtaacgtg actggcaaga gatattttta   2280
aaacaatgaa taggtttaca cttactttag ttttatggaa atgaaagatc atatcatata   2340
taatctagaa taaaattaac taaaataatt attatctaga taaaaaattt agaagccaat   2400
gaaatctata aataaactaa attaagtttta tttaattaac aactatggat ataaaatagg   2460
tactaatcaa aatagtgagg aggatatatt tgaatacata cgaacaaatt aataaagtga   2520
aaaaaatact tcgaaacat ttaaaaaata accttattgg tacttacatg tttggatcag   2580
gagttgagag tggactaaaa ccaaatagtg atcttgactt tttagtcgtc gtatctgaac   2640
cattgacaga tcaaagtaaa gaaatactta tacaaaaaat tagacctatt tcaaaaaaaa   2700
taggagataa aagcaactta cgatatattg aattaacaat tattattcag caagaaatgg   2760
taccgtggaa tcatcctccc aaacaagaat ttatttatgg agaatggtta caagagcttt   2820
atgaacaagg atacattcct cagaaggaat taaattcaga tttaaccata atgctttacc   2880
aagcaaaacg aaaaaataaa agaatatacg gaaattatga cttagaggaa ttactacctg   2940
atattccatt ttctgatgtg agaagagcca ttatggattc gtcagaggaa ttaatagata   3000
attatcagga tgatgaaacc aactctatat taactttatg ccgtatgatt ttaactatgg   3060
acacgggtaa aatcatacca aaagatattg cgggaaatgc agtggctgaa tcttctccat   3120
tagaacatag ggagagaatt ttgttagcag ttcgtagtta tcttggagag aatattgaat   3180
ggactaatga aaatgtaaat ttaactataa actatttaaa taacagatta aaaaaattat   3240 aaaaaattg aaaaaatggt ggaaacactt ttttcaattt ttttagatct tgagcaaaag   3300
gccagcaaaa ggccaggaac cgtaaaaagg ccgcgttgct ggcgtttttc cataggctcc   3360
gcccccctga cgagcatcac aaaaatcgac gctcaagtca gaggtggcga acccgacag   3420 gactataaag ataccaggcg tttccccctg gaagctccct cgtgcgctct cctgttccga   3480
```

```
ccctgccgct taccggatac ctgtccgcct ttctcccttc gggaagcgtg gcgctttctc    3540
atagctcacg ctgtaggtat ctcagttcgg tgtaggtcgt tcgctccaag ctgggctgtg    3600
tgcacgaacc ccccgttcag cccgaccgct gcgccttatc cggtaactat cgtcttgagt    3660
ccaacccggt aagacacgac ttatcgccac tggcagcagc cactggtaac aggattagca    3720
gagcgaggta tgtaggcggt gctacagagt tcttgaagtg gtggcctaac tacggctaca    3780
ctagaagaac agtatttggt atctgcgctc tgctgaagcc agttaccttc ggaaaaagag    3840
ttggtagctc ttgatccggc aaacaaacca ccgctggtag cggtggtttt tttgtttgca    3900
agcagcagat tacgcgcaga aaaaaaggat ctcaagaaga tcctttgatc ttttctacgg    3960
atccgtcttc ctgctggcct atgcattggg ttccgcagtg cccactccag gcggtctggg    4020
cggtgtggaa gcggcgctga cattcgcgtt cgtggcggtc ggagtgccgc agggcgtggc    4080
gctttccgcc actttgctgc accgcgtggt gttctactgg ctgcgcattc cgctgggcgc    4140
ggcggccatg aagtggcttg acaagcataa tcttgtctga ttcgtctatt ttcatacccc    4200
cttcggggaa atagatgtga aaaccctta t aaaacgcggg ttttcgcaga acatgcgct    4260 agtatcattg atgacaacat ggactaagca aaagtgcttg tccctgacc caagaaggat    4320 gcttt                                                                4325

<210> SEQ ID NO 34
<211> LENGTH: 1105
<212> TYPE: DNA
<213> ORGANISM: Artificial Sequence
<220> FEATURE:
<223> OTHER INFORMATION: expression cassett for pHuSP56L20-FGF2

<400> SEQUENCE: 34
gtcttcctgc tggcctatgc attgggttcc gcagtgccca ctccaggcgg tctgggcggt      60
gtggaagcgg cgctgacatt cgcgttcgtg gcggtcggag tgccgcaggg cgtggcgctt     120
tccgccactt tgctgcaccg cgtggtgttc tactggctgc gcattccgct gggcgcggcg     180
gccatgaagt ggcttgacaa gcataatctt gtctgattcg tctattttca taccccttc     240 ggggaaatag atgtgaaaac ccttataaaa cgcgggtttt cgcagaaaca tgcgctagta     300
tcattgatga acatggac taagcaaaag tgcttgtccc ctgacccaag aaggatgctt     360
tatgaaaaag aagaagacta tatcggctgc gctggcaaca cgttagcct taacctgcat     420 gggcagcggg ggaggtactg cgttcgcagt gccctgtct gatgctgact tgcagactt     480 ggcaagtcag attcagcaaa tcaacgatgc cgccggctcg atcaccaccc tgccggccct     540 gccgaggat ggcggctcgg cgccttccc gccgggccac ttcaaggacc cgaagcgcct     600
gtactgcaag aacggcggct tcttcctgcg tatccacccg gacggccgtg tggatggcgt     660
ccgtgagaag agcgacccgc atatcaagct gcagctgcag gccgaggaac gtggcgtggt     720
ctccatcaag ggcgtgtgcg ccaaccgcta cctggccatg aaggaagacg gccgtctgct     780
ggcctcgaag tgcgtcaccg atgaatgctt cttcttcgag cgcctggaat ccaacaacta     840
caacacctac cgctcccgta agtacaccag ctggtacgtg gccctgaagc gtaccggcca     900
gtacaagctg ggcagcaaga ccggcccggg ccagaaggcc atcctgttcc tgccgatgtc     960
cgccaagtcg caccaccacc atcatcattg accttctgct cgtagcgatt acttcgagca    1020
ttactgacga caaagacccc gaccgagatg gtcggggtct ttttgtttgtg gtgctgtgac    1080 gtgttgtcca accgtattat tccgg                                          1105
```

<210> SEQ ID NO 35
<211> LENGTH: 1117
<212> TYPE: DNA
<213> ORGANISM: Artificial Sequence
<220> FEATURE:
<223> OTHER INFORMATION: expression cassett for pHuSP67L20-FGF2

<400> SEQUENCE: 35

```
gtcttcctgc tggcctatgc attgggttcc gcagtgccca ctccaggcgg tctgggcggt      60
gtggaagcgg cgctgacatt cgcgttcgtg gcggtcggag tgccgcaggg cgtgcgcttt    120
tccgccactt tgctgcaccg cgtggtgttc tactggctgc gcattccgct gggcgcggcg    180
gccatgaagt ggcttgacaa gcataatctt gtctgattcg tctattttca taccccttc    240
ggggaaatag atgtgaaaac ccttataaaa cgcgggtttt cgcagaaaca tgcgctagta    300
tcattgatga caacatggac taagcaaaag tgcttgtccc ctgacccaag aaggatgctt    360
tatgaagata acaataagg caagggcgc tcttatcgcg caattaccg ccgcggcaac      420
gctattgtca tgcgggctgg ccgctgcaag tgccagtgcg gcaggtgtgg attacctgcc    480
taccatcggc caagtgccga catacaccaa gttccagccc gccgccggct cgatcaccac    540
cctgccggcc ctgccggagg atggcggctc gggcgccttc cgccgggcc acttcaagga     600
cccgaagcgc ctgtactgca gaacggcgg cttcttcctg cgtatccacc cggacggccg     660
tgtggatggc gtccgtgaga gagcgaccc gcatatcaag ctgcagctgc aggccgagga    720
acgtggcgtg gtctccatca agggcgtgtg cgccaaccgc tacctggcca tgaaggaaga    780
cggccgtctg ctggcctcga agtgcgtcac cgatgaatgc ttcttcttcg agcgcctgga    840
atccaacaac tacaacacct accgctcccg taagtacacc agctggtacg tggccctgaa    900
gcgtaccggc cagtacaagc tgggcagcaa gaccggcccg gccagaagg ccatcctgtt     960
cctgccgatg tccgccaagt cgtgaccttc tgctcgtagc gga                      1020
ttacttcgag cattactgac gacaaagacc ccgaccgaga tggtcggggt cttttgttg    1080
tggtgctgtg acgtgttgtc caaccgtatt attccgg                             1117
```

<210> SEQ ID NO 36
<211> LENGTH: 4307
<212> TYPE: DNA
<213> ORGANISM: Artificial Sequence
<220> FEATURE:
<223> OTHER INFORMATION: linear fragment of pHuSP26L20-FGF2-dHis

<400> SEQUENCE: 36

```
gccgccggct cgatcaccac cctgccggcc ctgccggagg atggcggctc gggcgccttc      60
cgccgggcc acttcaagga cccgaagcgc ctgtactgca gaacggcgg cttcttcctg     120
cgtatccacc cggacggccg tgtggatggc gtccgtgaga gagcgaccc gcatatcaag    180
ctgcagctgc aggccgagga acgtggcgtg gtctccatca agggcgtgtg cgccaaccgc    240
tacctggcca tgaaggaaga cggccgtctg ctggcctcga agtgcgtcac cgatgaatgc    300
ttcttcttcg agcgcctgga atccaacaac tacaacacct accgctcccg taagtacacc    360
agctggtacg tggccctgaa gcgtaccggc cagtacaagc tgggcagcaa gaccggcccg    420
gccagaagg ccatcctgtt cctgccgatg tccgccaagt cgtgaccttc tgctcgtagc     480
gattacttcg agcattactg acgacaaaga ccccgaccga gatggtcggg gtcttttgt    540
tgtggtgctg tgacgtgttg tccaaccgta ttattccgga ctagtcctcc aggacctcgt    600
ctacgaggcg ctgagcgagg aatggcgcaa aagggacggc gagatcagcg acccatgggc    660
```

```
caacgacgag gcggacggat accagccgcc ctcatacgag ccggtcaacc ccgaacgcag    720
gactccccag acgccctccg atggcctgat ctgacgtccg aaaaaaggcg ctgtgcgccc    780 ttttaaatc ttttataaat cttttacat tcttttagcc cctccgcagc cttactctcc      840
caacgggttt cagccgaaac ctacaccaaa aggggagcga acctacacca aaagggagc     900 gaacctacac caaaggggga gcgaacctac accaaaaggg gagctatata cacctttgt     960 tatttaaggt gcaagttgtg ctatgctgag gccatgtcca atgagatcgt gaagttcagc   1020
aaccagttca acaacgtcgc gctgaagaag ttcgacgccg tgcacctgga cgtgctcatg   1080
gcgatcgcct caagggtgag ggagaagggc acggccacgg tggagttctc gttcgaggag   1140
ctgcgcggcc tcatgcgatt gaggaagaac ctgaccaaca agcagctggc cgacaagatc   1200
gtgcagacga acgcgcgcct gctggcgctg aactacatgt tcgaggattc gggcaagatc   1260
atccagttcg cgctgttcac gaagttcgtc accgacccgc aggaggcgac tctcgcggtt   1320
ggggtcaacg aggagttcgc gttcctgctc aacgacctga ccagccagtt cacgcgcttc   1380
gagctggccg agttcgccga cctcaagagc aagtacgcca aggagttcta ccgcagggcc   1440
aagcagtacc gcagctccgg aatctggaag atcggccgcg acgagttctg ccgactgctt   1500
ggcgttccac cgtcggcaat aacccagaca cgatatctga atcagaaggt tcttcagcca   1560
attcaggagg agtgtgggcc tctccttggc ctgaagatcg agcgccagta cgtgaaacgc   1620
aggctgtcgg gcttcgtgtt cacattcgcc gcgagaccc tccggtgat cgacgccagg     1680 cccgtggagg cgaggaagac ggacggcgac ggcaagggcc attggacgag cgttgccggg   1740 tacgcgagg tgttcacgac cacggcgttg ttcgacgtga cggccgcccg ggctcacttc    1800
gacggcaccg ttgaagccgg ggagtgccgt ttctgcgcgt ttgacgcgcg caaccgcgaa   1860
catcatgcgc ggaacgccgg aaggctgttc tagcggccgt gtccgcgcct ctggggcggt   1920
tgcgcctgcc atgggtcgat ctgccgctgt tcggcctcac gctggtctgt gcgctgcctg   1980
atctccctga gcaggtcggc cttggtcctg ggggcgcttc gctcctcgaa cgggccgctc   2040
tcccccaggt cctcgggctc gctcaggtcc aacggctcgt caccggacgg ctcgggccgg   2100
ttctctccct gtgccgggtt ctccgcctgt gcgcgttgtt cggccatgcg cagtgcgagg   2160
gccttcacct gttcggggct tgtcgactcg atttcgttc gtgaatacat gttataataa   2220
ctataactaa taacgtaacg tgactggcaa gagatatttt taaaacaatg aataggttta   2280
cacttacttt agttttatgg aaatgaaaga tcatatcata tataatctag aataaaatta   2340
actaaaataa ttattatcta gataaaaaat ttagaagcca atgaaatcta taaataaact   2400
aaattaagtt tatttaatta acaactatgg atataaaata ggtactaatc aaaatagtga   2460
ggaggatata tttgaataca tacgaacaaa ttaataaagt gaaaaaaata cttcggaaac   2520
atttaaaaaa taaccttatt ggtacttaca tgtttggatc aggagttgag agtggactaa   2580
aaccaaatag tgatcttgac tttttagtcg tcgtatctga accattgaca gatcaaagta   2640
aagaaatact tatacaaaaa attagaccta tttcaaaaaa aataggagat aaaagcaact   2700
tacgatatat tgaattaaca attattattc agcaagaaat ggtaccgtgg aatcatcctc   2760
ccaaacaaga atttatttat ggagaatggt tacaagagct ttatgaacaa ggatacattc   2820
ctcagaagga attaaattca gatttaacca taatgcttta ccaagcaaaa cgaaaaaata   2880
aaagaatata cggaaattat gacttagagg aattactacc tgatattcca ttttctgatg   2940
tgagaagagc cattatggat tcgtcagagg aattaataga taattatcag gatgatgaaa   3000
ccaactctat attaacttta tgccgtatga ttttaactat ggacacgggt aaaatcatac   3060
```

```
caaaagatat tgcgggaaat gcagtggctg aatcttctcc attagaacat agggagagaa    3120
ttttgttagc agttcgtagt tatcttggag agaatattga atggactaat gaaaatgtaa    3180
atttaactat aaactatttta aataacagat taaaaaaatt ataaaaaaat tgaaaaaatg    3240
gtggaaacac tttttttcaat tttttttagat cttgagcaaa aggccagcaa aaggccagga    3300
accgtaaaaa ggccgcgttg ctggcgtttt tccataggct ccgcccccct gacgagcatc    3360
acaaaaatcg acgctcaagt cagaggtggc gaaacccgac aggactataa agataccagg    3420
cgtttccccc tggaagctcc ctcgtgcgct ctcctgttcc gaccctgccg cttaccggat    3480
acctgtccgc ctttctccct tcgggaagcg tggcgctttc tcatagctca cgctgtaggt    3540
atctcagttc ggtgtaggtc gttcgctcca agctgggctg tgtgcacgaa ccccccgttc    3600
agcccgaccg ctgcgcctta tccggtaact atcgtcttga gtccaacccg gtaagacacg    3660
acttatcgcc actggcagca gccactggta acaggattag cagagcgagg tatgtaggcg    3720
gtgctacaga gttcttgaag tggtggccta actacggcta cactagaaga acagtatttg    3780
gtatctgcgc tctgctgaag ccagttacct tcggaaaaag agttggtagc tcttgatccg    3840
gcaaacaaac caccgctggt agcggtggtt ttttgtttg caagcagcag attacgcgca    3900
gaaaaaaagg atctcaagaa gatcctttga tcttttctac ggatccgtct tcctgctggc    3960
ctatgcattg ggttccgcag tgcccactcc aggcggtctg gcggtgtgg aagcggcgct    4020 gacattcgcg ttcgtggcgg tcggagtgcc gcagggcgtg gcgctttccg ccactttgct    4080
gcaccgcgtg gtgttctact ggctgcgcat tccgctgggc gcggcggcca tgaagtggct    4140
tgacaagcat aatcttgtct gattcgtcta ttttcatacc cccttcgggg aaatagatgt    4200
gaaaaccctt ataaaacgcg gttttcgca gaaacatgcg ctagtatcat tgatgacaac    4260
atggactaag caaaagtgct tgtcccctga cccaagaagg atgcttt                  4307
```

<210> SEQ ID NO 37
<211> LENGTH: 3863
<212> TYPE: DNA
<213> ORGANISM: Artificial Sequence
<220> FEATURE:
<223> OTHER INFORMATION: pBEshuttle dna

<400> SEQUENCE: 37

```
ggatccgtct tcctgctggc ctatgcattg ggttccgcag tgcccactcc aggcggtctg      60
ggcggtgtgg aagcggcgct gacattcgcg ttcgtggcgg tcggagtgcc gcagggcgtg    120
gcgctttccg ccactttgct gcaccgcgtg gtgttctact ggctgcgcat tccgctgggc    180
gcggcggcca tgaagtggct tgacaagcat aatcttgtct gattcgtcta ttttcatacc    240
cccttcgggg aaatagatgt gaaaaccctt ataaaacgcg gttttcgca gaaacatgcg     300 ctagtatcat tgatgacaac atggactaag caaaagtgct tgtcccctga cccaagaagg    360
atgctttatg aagcttatcc tgcagtgacc ttctgctcgt agcgattact tcgagcatta    420
ctgacgacaa agaccccgac cgagatgtc ggggtctttt tgttgtggtg ctgtgacgtg     480
ttgtccaacc gtattattcc ggactagtcc tccaggacct cgtctacgag gcgctgagcg    540
aggaatggcg caaagggac ggcgagatca gcgacccatg ggccaacgac gaggcggacg     600
gataccagcc gccctcatac gagccggtca accccgaacg caggactccc cagacgccct    660
ccgatggcct gatctgacgt ccgaaaaaag gcgctgtgcg cccttttaa atcttttata     720 aatctttta cattcttta gccccctccgc agccttactc tcccaacggg tttcagccga    780
aacctacacc aaaaggggag cgaacctaca ccaaaagggg agcgaaccta caccaaaagg    840
```

```
ggagcgaacc tacaccaaaa ggggagctat atacaccttt tgttatttaa ggtgcaagtt      900
gtgctatgct gaggccatgt ccaatgagat cgtgaagttc agcaaccagt tcaacaacgt      960
cgcgctgaag aagttcgacg ccgtgcacct ggacgtgctc atggcgatcg cctcaagggt     1020
gagggagaag ggcacggcca cggtggagtt ctcgttcgag gagctgcgcg gcctcatgcg     1080
attgaggaag aacctgacca caagcagct ggccgacaag atcgtgcaga cgaacgcgcg      1140
cctgctggcg ctgaactaca tgttcgagga ttcgggcaag atcatccagt tcgcgctgtt     1200
cacgaagttc gtcaccgacc gcaggaggc gactctcgcg gttggggtca acgaggagtt      1260
cgcgttcctg ctcaacgacc tgaccagcca gttcacgcgc ttcgagctgg ccgagttcgc     1320
cgacctcaag agcaagtacg ccaaggagtt ctaccgcagg gccaagcagt accgcagctc     1380
cggaatctgg aagatcggcc gcgacgagtt ctgccgactg cttggcgttc caccgtcggc     1440
aataacccag acacgatatc tgaatcagaa ggttcttcag ccaattcagg aggagtgtgg     1500
gcctctcctt ggcctgaaga tcgagcgcca gtacgtgaaa cgcaggctgt cgggcttcgt     1560
gttcacattc gcccgcgaga cccctccggt gatcgacgcc aggcccgtgg aggcgaggaa     1620
gacggacggc gacggcaagg gccattggac gagcgttgcc gggtacggcg aggtgttcac     1680
gaccacggcg ttgttcgacg tgacggccgc ccgggctcac ttcgacggca ccgttgaagc     1740
cggggagtgc cgtttctgcg cgtttgacgc gcgcaaccgc gaacatcatg cgcggaacgc     1800
cggaaggctg ttctagcggc cgtgtccgcg cctctgggc ggttgcgcct gccatgggtc      1860
gatctgccgc tgttcggcct cacgctggtc tgtgcgctgc ctgatctccc tgagcaggtc     1920
ggccttggtc ctgggggcgc ttcgctcctc gaacgggccg ctctccccca ggtcctcggg     1980
ctcgctcagg tccaacggct cgtcaccgga cggctcgggc cggttctctc cctgtgccgg     2040
gttctccgcc tgtgcgcgtt gttcggccat gcgcagtgcg agggccttca cctgttcggg     2100
gcttgtcgac tcgattttcg ttcgtgaata catgttataa aactataac taataacgta      2160
acgtgactgg caagagatat ttttaaaaca atgaataggt ttacacttac tttagttta      2220
tggaaatgaa agatcatatc atatataatc tagaataaaa ttaactaaaa taattattat     2280
ctagataaaa aatttagaag ccaatgaaat ctataaataa actaaattaa gtttatttaa     2340
ttaacaacta tggatataaa ataggtacta atcaaaatag tgaggaggat atatttgaat     2400
acatacgaac aaattaataa agtgaaaaaa atacttcgga aacatttaaa aaataacctt     2460
attggtactt acatgtttgg atcaggagtt gagagtggac taaaaccaaa tagtgatctt     2520
gactttttag tcgtcgtatc tgaaccattg acagatcaaa gtaaagaaat acttatacaa     2580
aaaattagac ctatttcaaa aaaaatagga gataaaagca acttacgata tattgaatta     2640
acaattatta ttcagcaaga aatggtaccg tggaatcatc ctcccaaaca agaatttatt     2700
tatggagaat ggttacaaga gctttatgaa caaggataca ttcctcagaa ggaattaaat     2760
tcagatttaa ccataatgct ttaccaagca aaacgaaaaa ataaaagaat atacggaaat     2820
tatgacttag aggaattact acctgatatt ccatttctg atgtgagaag agccattatg       2880
gattcgtcag aggaattaat agataattat caggatgatg aaaccaactc tatattaact     2940
ttatgccgta tgattttaac tatggacacg ggtaaaatca taccaaaaga tattgcggga     3000
aatgcagtgg ctgaatcttc tccattagaa cataggagga gaattttgtt agcagttcgt     3060
agttatcttg gagagaatat tgaatggact aatgaaaatg taaatttaac tataaactat     3120
ttaaataaca gattaaaaaa attataaaaa aattgaaaaa atggtggaaa cacttttttc     3180
aatttttta gatcttgagc aaaaggccag caaaaggcca ggaaccgtaa aaaggccgcg      3240
```

```
ttgctggcgt ttttccatag gctccgcccc cctgacgagc atcacaaaaa tcgacgctca    3300
agtcagaggt ggcgaaaccc gacaggacta taaagatacc aggcgtttcc ccctggaagc    3360
tccctcgtgc gctctcctgt tccgaccctg ccgcttaccg gatacctgtc cgcctttctc    3420
ccttcgggaa gcgtggcgct ttctcatagc tcacgctgta ggtatctcag ttcggtgtag    3480
gtcgttcgct ccaagctggg ctgtgtgcac gaaccccccg ttcagcccga ccgctgcgcc    3540
ttatccggta actatcgtct tgagtccaac ccggtaagac acgacttatc gccactggca    3600
gcagccactg gtaacaggat tagcagagcg aggtatgtag gcggtgctac agagttcttg    3660
aagtggtggc ctaactacgg ctacactaga agaacagtat ttggtatctg cgctctgctg    3720
aagccagtta ccttcggaaa aagagttggt agctcttgat ccggcaaaca aaccaccgct    3780
ggtagcggtg gtttttttgt ttgcaagcag cagattacgc gcagaaaaaa aggatctcaa    3840
gaagatcctt tgatcttttc tac                                            3863

<210> SEQ ID NO 38
<211> LENGTH: 114
<212> TYPE: DNA
<213> ORGANISM: Artificial Sequence
<220> FEATURE:
<223> OTHER INFORMATION: Hu terminator

<400> SEQUENCE: 38
ccttctgctc gtagcgatta cttcgagcat tactgacgac aaagacccccg accgagatgg     60 tcggggtctt tttgttgtgg tgctgtgacg tgttgtccaa ccgtattatt ccgg           114
```

THERAPEUTIC AGENT FOR ISCHEMIC DISEASES

RELATED APPLICATION

This application is a national stage filing under 35 U.S.C. § 371 of International Application No. PCT/JP2016/051293, filed Jan. 18, 2016, entitled "Therapeutic Agent for Ischemic Diseases," the contents of which is incorporated by reference herein in its entirety.

TECHNICAL FIELD

The present invention relates to a novel secretory signal, a transformation plasmid containing the secretory signal, a gene transport carrier formed from an anaerobic bacterium transformed by the plasmid, a pharmaceutical composition containing the gene transport carrier, and a method for diagnosing or treating an ischemic disease using same.

BACKGROUND ART

In recent years, with regard to methods for treating malignant tumors, a method in which a transformed anaerobic bacterium is used as a gene transport carrier has been attracting attention, and for example a method in which a gene expressing a nitroreductase, which is an enzyme that converts a prodrug for an anti-tumor substance into the anti-tumor substance, is transported to a tumor site using a transformed *clostridium* has been proposed (ref. Patent Documents 1 to 3).

However, all of the microorganisms that have conventionally been used for this purpose are ones formed by mutating a pathogenic microbe so that it has low toxicity, and the possibility that it will return to the original pathogenic microbe by reverse mutation and exhibit toxicity cannot be ruled out; furthermore, there is a possibility that the effect will be exhibited not only in diseased tissue but also in normal tissue due to mobility and invasiveness to thus cause systemic side effect symptoms, and there is thus a problem in terms of safety.

Under such circumstances, *Bifidobacterium*, which is a nonpathogenic enterobacterium that is present within and makes up the flora of the human intestines and is known to be a very safe obligate anaerobic bacterium, has been attracting attention, and a transformed *Bifidobacterium* that expresses cytosine deaminase, which is an enzyme that converts the prodrug 5-fluorocytosine for the anti-tumor substance 5-fluorouracil into 5-FU, and a transformed *Bifidobacterium* that expresses TNFα, which is an anti-tumor protein, have been developed (Ref. Patent Documents 4 to 6).

This transformed *Bifidobacterium* has the characteristics that, when intravenously administered to an animal model with a solid tumor, which is an anaerobic disease, it specifically colonizes and grows in anaerobic diseased tissue in a low oxygen state and quickly disappears in normal tissue that is not in an anaerobic environment (Ref. Non-Patent Documents 1 and 2).

On the other hand, in the treatment of an ischemic disease, in particular in the treatment of serious ischemia, an angiogenic therapy in which blood flow is restored by regeneration of blood vessels or development of collateral circulation has been attempted. Angiogenic therapy can be broadly divided into three types of therapies, that is, cell transplantation, protein administration, and gene therapy, but from the viewpoint of low invasiveness gene therapy has particularly been attracting attention in recent years. In angiogenesis by gene therapy, for example, a gene encoding hepatocyte growth factor (hepatocyte growth factor: HGF), vascular endothelial growth factor (vascular endothelial growth factor: VEGF), etc. is introduced into the vicinity of an affected area by intramuscular injection or intraarterial infusion, thus promoting angiogenesis in the vicinity of the affected area to thereby restore blood flow (e.g. Ref. Non-Patent Documents 3 and 4).

These angiogenic therapies have been attracting attention as one option for a patient for whom revascularization is not possible due to a disorder at the arteriolar level or for whom the effect is insufficient, a patient for whom surgical treatment cannot be carried out due to a problem with invasiveness, etc., and in recent years many clinical trials involving angiogenic therapy by gene therapy in particular have been carried out.

However, since angiogenic therapy employing conventional gene therapy does not have specificity for a lesion site, systemic administration is impossible, and there is concern for the steal effect, in which angiogenesis is promoted in a non-ischemic site rather than in an ischemic site; control of the efficiency of gene transfer and the period of expression of the transgene is difficult, there is a large risk when a patient has complications giving symptoms that can be exacerbated by angiogenesis, and there are still a large number of problems to be solved before the therapy can be applied.

Therefore, the present inventors have focused attention on anaerobic bacteria that colonize and grow specifically in anaerobic diseased tissue, and have successfully prepared, by the use of a transformed *Bifidobacterium*, a gene transport carrier that specifically accumulates only in an ischemic site, produces a desired protein only in the ischemic site, and disappears from the lesion site when it is cured, thus stopping production of the protein (Patent Document 7).

PRIOR ART DOCUMENTS

Patent Documents

[Patent Document 1] U.S. Pat. No. 6,416,754
[Patent Document 2] U.S. Pat. No. 6,652,849
[Patent Document 3] US Patent Application No. 2003/0103952
[Patent Document 4] JP, A, 2002-97144
[Patent Document 5] International Patent Application WO2007/136107
[Patent Document 6] International Patent Application WO2011/093465
[Patent Document 7] International Patent Application WO2013/008881

Non-Patent Documents

[Non-Patent Document 1] Yazawa et al., Cancer Gene Therapy, 7 (2): 269-274, 2000.
[Non-Patent Document 2] Yazawa et al., Breast Cancer Research and Treatment, 66: 165-170, 2001.
[Non-Patent Document 3] Gupta et al., Circ. Res., 105: 724-736, 2009.
[Non-Patent Document 4] Morishita et al., Arterioscler Thromb Vasc Biol., 31: 713-720, 2011.

SUMMARY OF THE INVENTION

Problems to be Solved by the Invention

The object of the present invention is to provide a transformation plasmid for transforming an anaerobic bacterium in order to enable a target protein to be stably expressed and secreted at high efficiency, a gene transport carrier formed from an anaerobic bacterium transformed with the plasmid, a pharmaceutical composition containing the gene transport carrier, and a method for diagnosing or treating an ischemic disease utilizing same.

Means for Solving the Problems

The present inventors have reported in Patent Document 7 above the preparation of transformation plasmid pFGF12a having incorporated thereinto a gene encoding human FGF2, that an obligate anaerobic bacterium transformed using same, such as for example *Bifidobacterium longum* 105A/pFGF12a or *Bifidobacterium breve* JCM1192/pFGF12a, accumulates and grows specifically only at a site of ischemic disease by systemic administration, and that human FGF2 protein can be expressed and secreted at the site of ischemic disease (Patent Document 7).

However, while continuing further research, a new problem has been encountered in that the amount of expressed protein secreted by the *Bifidobacterium* transformed with transformation plasmid pFGF12a, which is mainly used in Patent Document 7 above, is not sufficient, and the amount secreted decreases over time, there thus being a lack of stability.

As a result of an intensive investigation by the present inventors in order to solve the above problems, novel secretory signal peptides SP56 and SP67 derived from *Bifidobacterium longum* have been found; when a plasmid having incorporated thereinto a gene encoding these signal peptides is prepared, an anaerobic bacterium transformed with the plasmid surprisingly has exceptionally high protein expression/secretion compared with existing strains, expressed protein can be stably secreted during long-term culturing, the plasmid is one for which a high percentage of bacteria retaining the plasmid is shown even after repeated passage culture, and as a result of further research the present invention has been accomplished.

That is, the present invention relates to the following.
(1) A transformation plasmid for an anaerobic bacterium, the plasmid comprising a promoter unit, a secretory signal unit comprising DNA encoding a secretory signal peptide represented by SEQ ID No: 1 or SEQ ID No: 2, and a target gene unit comprising DNA encoding a protein useful for the diagnosis or treatment of an ischemic disease.
(2) The transformation plasmid according to (1), wherein the protein useful for the diagnosis or treatment of an ischemic disease is one type selected from the group consisting of a protein having angiogenesis promoting activity such as fibroblast growth factor (FGF), endothelial cell growth factor (ECGF), vascular endothelial growth factor (VEGF), hepatocyte growth factor (HGF), vascular growth factor (AGF), platelet-derived growth factor (PDGF), transforming growth factor β (TGFβ), angiopoietin or ephrin; a factor involved in vasodilation such as a prostaglandin; a colony stimulating factor such as granulocyte colony stimulating factor (G-CSF) or granulocyte-macrophage colony stimulating factor (GM-CSF); nerve growth factor (NGF); brain-derived neurotrophic factor (BDNF); a neurotrophin such as neurotrophin 3; insulin-like growth factor (IGF); and platelet-derived vascular endothelial cell growth factor (PD-ECGF).
(3) The transformation plasmid according to (1) or (2), wherein the protein useful for the diagnosis or treatment of an ischemic disease is fibroblast growth factor 2 (FGF2).

(4) The transformation plasmid according to (1) to (3), wherein the secretory signal unit further comprises DNA encoding a spacer peptide continuing from the 3' terminal of the DNA encoding a secretory signal peptide represented by SEQ ID No: 1 or SEQ ID No: 2.
(5) The transformation plasmid according to (4), wherein the spacer peptide has a length of 1 to 25 amino acids, and is represented by a sequence starting from the N terminal amino acid of an amino acid sequence represented by SEQ ID No: 5 or SEQ ID No: 6.
(6) The transformation plasmid according to (1) to (5), wherein the secretory signal unit is DNA encoding an amino acid sequence represented by SEQ ID No: 9 or SEQ ID No: 10.
(7) The transformation plasmid according to (1) to (6), wherein the transformation plasmid is a non-shuttle plasmid.
(8) The transformation plasmid according to (1) to (7), wherein a promoter contained in the promoter unit is a base sequence represented by SEQ ID No: 13 or a sequence formed by deletion, substitution, or addition of one or a plurality of bases of the base sequence.
(9) The transformation plasmid according to (1) to (8), wherein the transformation plasmid is represented by the base sequence of pFGF110 (SEQ ID No: 14) or pFGF111 (SEQ ID No: 15).
(10) A gene transport carrier comprising an anaerobic bacterium transformed with the transformation plasmid according to (1) to (9).
(11) The gene transport carrier according to (10), wherein the anaerobic bacterium is a *Bifidobacterium*.
(12) The gene transport carrier according to (11), wherein the *Bifidobacterium* is *Bifidobacterium longum*.
(13) A pharmaceutical composition comprising the gene transport carrier according to (10) to (12).
(14) The pharmaceutical composition according to (13), wherein the pharmaceutical composition further comprises an agent for promoting colonization and growth of the gene transport carrier at the site of an ischemic disease.
(15) The pharmaceutical composition according to (14), wherein the agent for promoting colonization and growth is at least one type selected from the group consisting of maltose, lactulose, arabinose, xylose, galactose, glucose, lactose, melibiose, melezitose, and raffinose.
(16) A method for diagnosing or treating an ischemic disease, the method comprising administering the gene transport carrier according to (10) to (12).
(17) The method according to (16), wherein said administration is systemic administration.

Effects of the Invention

The transformation plasmid of the present invention is a novel plasmid that has a novel secretory signal and is useful for preparing a transformed anaerobic bacterium for diagnosing and/or treating an ischemic disease, and an anaerobic bacterium transformed with the transformation plasmid of the present invention can stably secrete a large amount of target protein.

Since the gene transport carrier of the present invention is formed by an anaerobic bacterium transformed with the transformation plasmid of the present invention, even when it is administered systemically, it colonizes and grows specifically at the site of an ischemic disease, which is in an anaerobic environment, and sufficient protein having therapeutic activity for the ischemic disease can be produced and secreted at the disease site. It is therefore extremely useful as a gene transport carrier, and consequently as an ischemic disease treatment agent. Furthermore, since it specifically colonizes at the site of an ischemic disease, it accumulates specifically at the site of an ischemic disease and exhibits the effect even in the case of systemic administration such as intravenous injection. Therefore, administration of a large amount or administration a plurality of times is not needed, and the burden on the subject of administration can be alleviated. Moreover, since the anaerobic environment of the site of an ischemic disease is maintained while the ischemia persists, there is growth for a long period of time, but once the ischemia is cured the anaerobic environment is lost, growth is not possible and there is rapid disappearance.

Furthermore, with regard to the gene transport carrier of the present invention, since the gene transport carrier itself can express a protein useful for treatment, unlike conventional methods it is unnecessary to take into consideration the efficiency of gene transfer to cells at the ischemic site or the vicinity thereof, and a high protein expression efficiency can always be exhibited. Furthermore, since it is a carrier delivered specifically to the ischemic site, there is little possibility of complications. Therefore, an angiogenesis treatment having lower invasiveness, fewer side effects, and higher safety can be provided compared with conventional methods. Moreover, by making a marker be expressed at the same time the gene transport carrier of the present invention can be used as a monitor for the diagnosis or treatment of an ischemic site. Furthermore, the gene transport carrier of the present invention can deliver a plurality of genes at the same time, and by incorporating and administering a plurality of effective growth factors it can be expected that a more efficient and noninvasive treatment will become possible.

MODES FOR CARRYING OUT THE INVENTION

Figure 1:
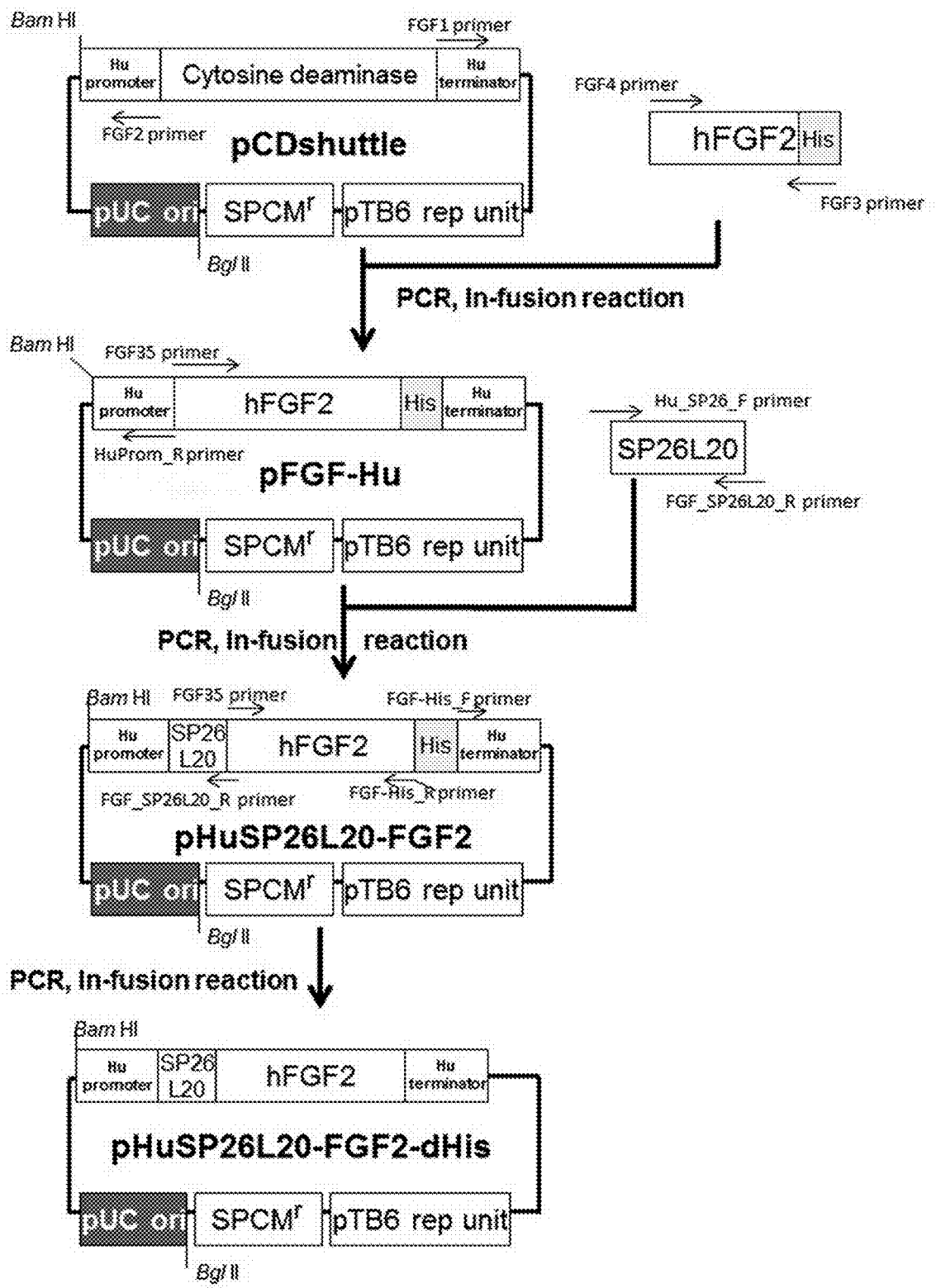
FIG. 1 shows a schematic diagram relating to preparation of a human FGF2 secreting shuttle plasmid. pFGF-Hu is prepared from a pCD shuttle plasmid by replacing CD with hFGF2 (with His tag), pHuSP26L20-FGF2 is further prepared by inserting SP26L20 between the promoter and the hFGF2 gene, and pHuSP26L20-FGF2-dHis is prepared by removing the His tag therefrom.
Figure 2:
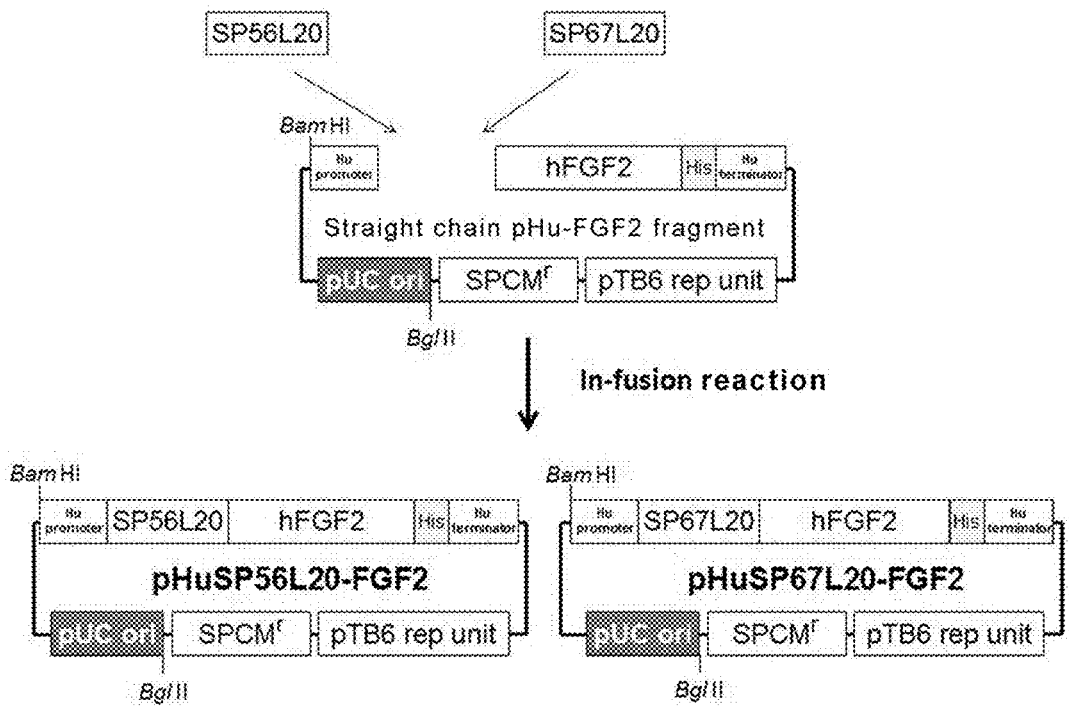
FIG. 2 shows a schematic diagram relating to preparation of a human FGF2 (with tag) secreting shuttle plasmid. pHuSP56L20-FGF2 and pHuSP67L20-FGF2 are prepared by inserting SP56L20 and SP67L20 respectively into a straight chain pHu-FGF2 fragment.
Figure 3:
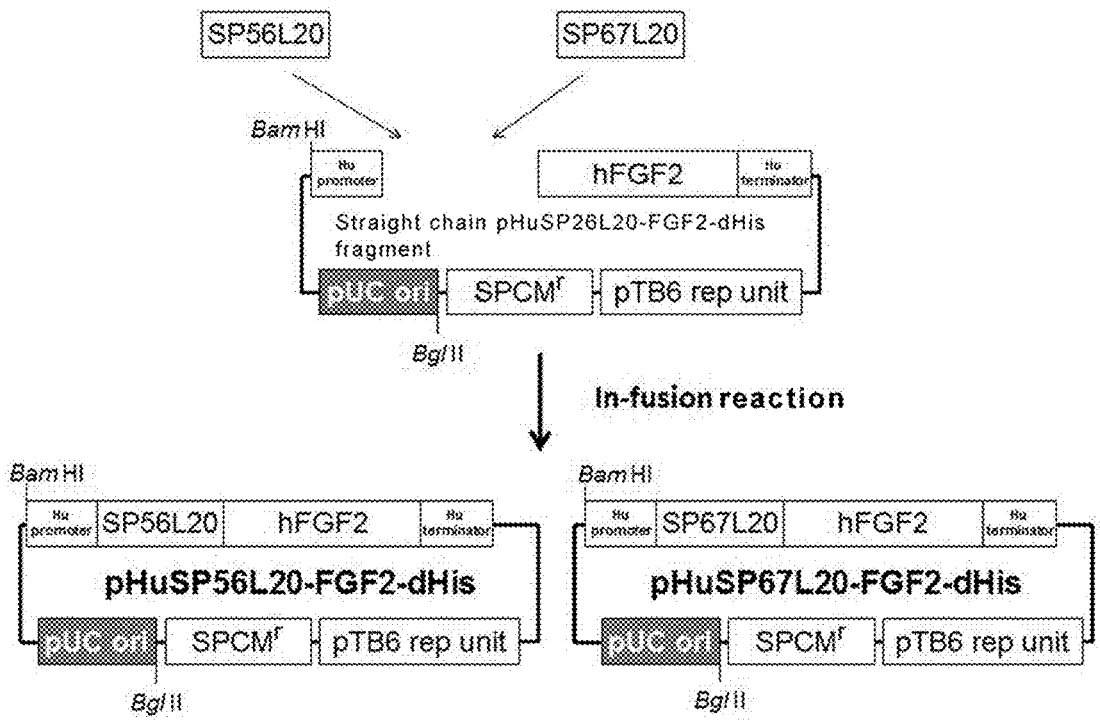
FIG. 3 shows a schematic diagram relating to preparation of a human FGF2 (no tag) secreting shuttle plasmid. pHuSP56L20-FGF2-dHis and pHuSP67L20-FGF2-dHis are prepared by inserting SP56L20 and SP67L20 respectively into a straight chain pHuSP26L20-FGF2-dHis fragment.
Figure 4:
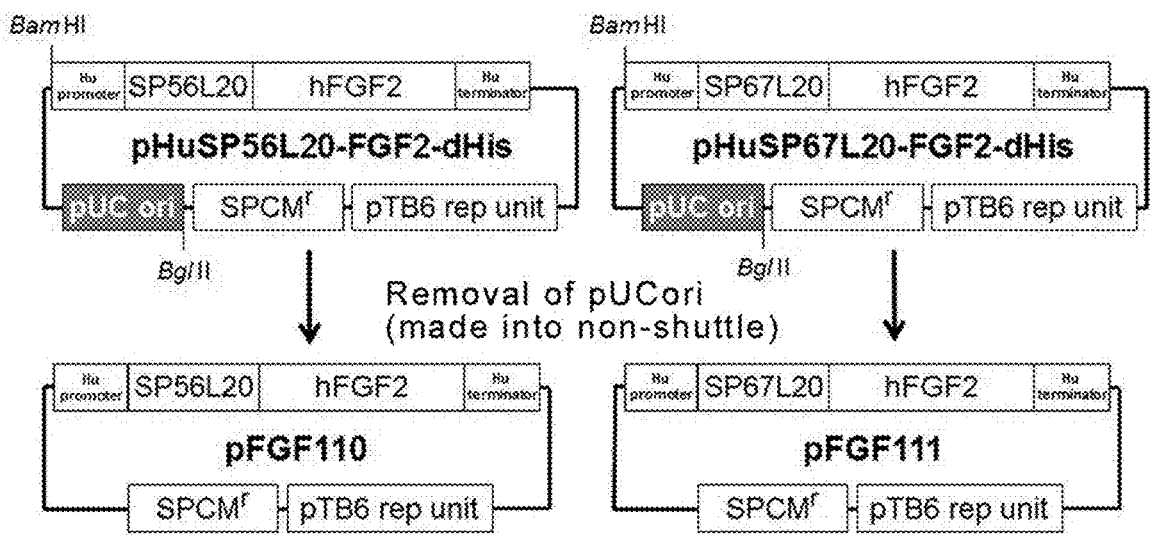
FIG. 4 shows a schematic diagram relating to preparation of a human FGF2 (no tag) secreting non-shuttle plasmid. pFGF110 and pFGF111 are prepared by removing pUCori from pHuSP56L20-FGF2-dHis and pHuSP67L20-FGF2-dHis respectively.

The present invention relates to a novel secretory signal peptide derived from a *Bifidobacterium*, a secretory signal encoding the peptide, and a transformation plasmid, etc. containing the secretory signal.

The present invention is explained in detail below.
<Transformation Plasmid>

The transformation plasmid of the present invention enables to more stably secrete more expressed protein due to the action of a novel secretory signal unit and therefore can be characterized in that by using the same, a highly useful transformed anaerobic bacterium expressing and secreting any target protein with high efficiency can be prepared.

In one aspect, the present invention relates to a transformation plasmid for transforming an anaerobic bacterium, the plasmid comprising a promoter unit, a secretory signal unit comprising DNA encoding a secretory signal peptide represented by SEQ ID No: 1 or SEQ ID No: 2, and a target gene unit comprising DNA encoding a protein useful for the diagnosis or treatment of an ischemic disease (target protein).

In the present specification, 'anaerobic bacterium' means a bacterium having anaerobic properties, and 'anaerobic properties' means properties of being able to grow under conditions where there is little or no oxygen. In general, anaerobic bacteria can be classified into facultative anaerobic bacteria, which can also grow in the presence of oxygen, and obligate anaerobic bacteria, which cannot grow in the presence of oxygen, but in one embodiment of the present invention, an obligate anaerobic bacterium such as for example a *Bifidobacterium* is preferable. The anaerobic properties possessed by the anaerobic bacterium of the present invention may be properties intrinsically possessed by the bacterium or those obtained by mutations such as spontaneous mutation or transformation. Therefore, in one embodiment of the present invention, the anaerobic bacterium is one mutated so as to be an obligate anaerobic bacterium. For example, it can be a facultative anaerobic bacterium such as *Lactobacillus* as long as it is one that has been mutated so as to be obligately anaerobic.

In a preferred embodiment, the transformation plasmid of the present invention is for transforming a *Bifidobacterium* and, furthermore, in a preferred embodiment for transforming *Bifidobacterium longum*.

In the present specification, 'expression cassette' means a set of genes, contained in the plasmid, for expressing a specific protein or peptide fragment, and this set contains a promoter unit and a target gene unit and may further contain any other useful unit. Examples of said other useful unit include a gene encoding a signal peptide such as a secretory signal and a gene encoding a molecular chaperone for a protein encoded by the target gene.

In the present specification, the 'target gene unit', including a gene encoding the target protein (expressed protein), means a set of genes related to the expressed protein. The target gene unit may contain other DNA than the gene encoding the target protein. Examples of said other DNA that can be contained in the target gene unit include, but are not limited to, DNA encoding a peptide that labels an expressed protein, such as His-Tag.

The plasmid of the present invention contains a secretory signal unit so that a protein encoded by the transformation plasmid of the present invention is produced within an anaerobic bacterial cell and released outside the bacterial cell to thus exhibit a therapeutic effect.

In the present specification, 'secretory signal unit' means a set of genes encoding an amino acid sequence, including a secretory signal sequence, for secreting an expressed protein outside a bacterial cell. In the present specification, when simply a 'secretory signal' is referred to or when a 'secretory signal sequence' is referred to, it means a gene encoding a secretory signal peptide or a DNA sequence thereof. The secretory signal unit may contain, as well as a secretory signal sequence, for example, other DNA such as DNA encoding a spacer peptide inserted between the target gene and the secretory signal sequence.

The secretory signal sequence contained in the secretory signal unit of the present invention is a sequence encoding a novel secretory signal peptide represented by SP56 (SEQ ID No: 1) or SP67 (SEQ ID No: 2). In addition, the secretory signal sequences corresponding to secretory signal peptide sequences represented by SEQ ID No: 1 and SEQ ID No: 2 include, in addition to those represented by SEQ ID No: 3 and SEQ ID No: 4 respectively, a degenerate sequence thereof. Hereinafter in the present specification, when 'DNA encoding' an amino acid sequence or a 'base sequence corresponding' to an amino acid sequence is referred to, unless otherwise specified it is intended to contain, in addition to the specific sequence shown as an example, a degenerate sequence thereof.

The novel secretory signal peptide represented by SP56 (SEQ ID No: 1) or SP67 (SEQ ID No: 2) is a secretory signal peptide further selected from candidates abstracted using a secretory signal peptide prediction program from the entire amino acid sequence registered in the genome database of *Bifidobacterium longum*, and is confirmed for the first time by the present inventors that it is a useful secretory signal peptide.

The secretory signal peptides SP56 and SP67 of the present invention have particularly excellent secretory activity, and since they function in a *Bifidobacterium*, which is a nonpathogenic obligate anaerobic bacterium, DNA encoding SP56 and SP67 is particularly suitable for use in a transformation plasmid for an anaerobic bacterium for the diagnosis or treatment of an anaerobic disease, in particular an ischemic disease. Therefore, any transformation plasmid containing DNA encoding SP56 and SP67 is also included in the present invention.

In one embodiment, the target gene unit of the present invention contains DNA encoding a protein useful for the diagnosis or treatment of an ischemic disease as an expressed protein.

In the present specification, 'ischemia' means a state in which the tissue is short of oxygen and nutrients due to the flow of blood in arteries supplying the tissue being reduced by the constriction or occlusion of blood vessels, and persistent ischemia causes atrophy, degeneration, or necrosis of the tissue.

The transformation plasmid of the present invention is suitably used in a treatment method for improving an undesirable state caused by ischemia, mainly in an angiogenesis treatment, protection of an organ, and so on. Therefore, 'ischemic disease' in the present specification means a state in which ischemia of the tissue persists due to arterial constriction or occlusion irrespective of the presence or absence of subjective symptoms, or an undesirable state caused by such ischemia. Examples of the ischemic disease include, but are not limited to, an ischemic heart disease such as angina pectoris or myocardial infarction, a cerebral ischemic disease such as cerebral infarction, a chronic cerebral ischemic disease such as moyamoya disease, a spinal ischemic disease, an ischemic colitis, an ischemic bowel disease such as mesenteric arterial occlusion, a lower limb ischemic disease such as arteriosclerosis obliterans or Buerger's disease, and a retinal ischemic disease such as diabetic retinopathy.

An 'ischemic site' in the present specification means the site of a state in which the arterial blood flow, nutrients, and oxygen are reduced due to ischemia, and it can be used interchangeably with 'site of ischemic disease' or 'ischemic diseased tissue'.

Examples of the protein useful for the diagnosis or treatment of an ischemic disease include, but are not limited to, a protein having angiogenesis promoting activity and a protein involved in vasodilation. Examples of the protein having angiogenesis promoting activity include, but are not limited to, fibroblast growth factor (FGF), endothelial cell growth factor (ECGF), vascular endothelial growth factor (VEGF), hepatocyte growth factor (HGF), vascular growth factor (AGF), platelet-derived growth factor (PDGF), transforming growth factor β (TGFβ), angiopoietin, and ephrin, and examples of the factor involved in vasodilation include a prostaglandin. Further examples of the protein useful for treatment include a colony stimulating factor (e.g. granulocyte colony stimulating factor (G-CSF), a granulocyte-macrophage colony stimulating factor (GM-CSF), etc.), nerve growth factor (NGF), brain-derived neurotrophic factor (BDNF), a neurotrophin (e.g. neurotrophin 3, etc.), insulin-like growth factor (IGF), and platelet-derived vascular endothelial cell growth factor (PD-ECGF). The protein useful for the diagnosis or treatment of an ischemic disease is particularly preferably fibroblast growth factor 2 (FGF2).

In the present invention, the 'promoter unit' means a unit containing a promoter and any other region involved in transcription control, and examples of said other region involved in transcription control include an operator and a terminator.

The promoter contained in the promoter unit of the present invention may be any promotor as long as it functions in an anaerobic bacterium, and examples thereof include a promoter positioned upstream of the *Bifidobacterium*-derived secretory signal and a promoter (Hu promoter) for a gene encoding a histone-like DNA-binding protein that functions in a *Bifidobacterium*. In one embodiment, the promoter contained in the promoter unit of the present invention may be for example Hu promoter (SEQ ID No: 13) or P37 promoter (SEQ ID No: 16), and it is preferably Hu promoter. The promoter contained in the promoter unit of the present invention may be represented by one formed by deletion, substitution, or addition of one or a plurality of bases of the base sequence thereof (functional equivalent) as long as the function as a promoter is maintained.

In one embodiment of the present invention, the promoter unit contains a terminator. Any terminator may be contained as long as it functions in a *Bifidobacterium*, but it is preferably a terminator (Hu terminator) for a gene encoding a histone-like DNA-binding protein that functions in a *Bifidobacterium*, and is most preferably DNA represented by the base sequence of SEQ ID No: 38 in particular or one formed by deletion, substitution, or addition of one or a plurality of bases thereof.

In one embodiment of the present invention, the secretory signal unit further contains DNA encoding a spacer peptide continuing from the 3' terminal of the DNA encoding the secretory signal peptide.

In the present specification, the 'spacer peptide' is a peptide inserted between the secretory signal peptide and the N terminal of the target protein. Therefore, the DNA encoding the spacer peptide is DNA that is present downstream of the secretory signal and upstream of the gene encoding the target protein in the expression cassette.

The presence of the spacer peptide increases the secretion efficiency of the target protein. Therefore, in a preferred embodiment, the spacer peptide has a length of 1 to 25 amino acids, preferably a length of 1 to 20 amino acids, and more preferably a length of 5 to 20 amino acids. The sequence of the spacer peptide is not particularly limited, but in the case of SP56 it is preferably a peptide represented by SEQ ID No: 5 or a partial peptide that contains the N terminal thereof, and in the case of SP67 it is a peptide represented by SEQ ID No: 6 or a partial peptide that contains the N terminal thereof.

SEQ ID Nos: 5 and 6 are peptides comprising a sequence from the N terminal to the $25^{th}$ amino acid of a protein secreted by SP56 and SP67 respectively in *Bifidobacterium longum*. In the above preferred embodiment, for example, in the case of SP56 the spacer peptide of the present invention may be a peptide represented by a partial sequence formed from only the $1^{st}$ amino acid of the peptide represented by SEQ ID No: 5 and having a length of one amino acid, a partial sequence from the $1^{st}$ to $15^{th}$ amino acids of SEQ ID No: 5 and having a length of 15 amino acids, a partial sequence from the $1^{st}$ amino acid to the $20^{th}$ amino acid of SEQ ID No: 5 and having a length of 20 amino acids, or the complete sequence of SEQ ID No: 5, which has a length of 25 amino acids, and in the case of SP67 it may be a peptide represented by a partial sequence formed only from the $1^{st}$ amino acid of the peptide represented by SEQ ID No: 6 and having a length of one amino acid, a partial sequence from the $1^{st}$ amino acid to the $15^{th}$ amino acid of SEQ ID No: 6 and having a length of 15 amino acids, a partial sequence from the $1^{st}$ amino acid to $20^{th}$ amino acid of SEQ ID No: 6 and having a length of 20 amino acids, or the complete sequence of SEQ ID No: 6, which has a length of 25 amino acids.

In addition, the base sequences corresponding to the amino acid sequences represented by SEQ ID No: 5 and SEQ ID No: 6 are preferably those represented by SEQ ID No: 7 and SEQ ID No: 8 respectively.

In a more preferred embodiment of the present invention, the secretory signal unit is DNA encoding the amino acid sequence represented by SEQ ID No: 9 and formed from SP56 and a spacer peptide having 20 amino acids, or the amino acid sequence represented by SEQ ID No: 10 and formed from SP67 and a spacer peptide having 20 amino acids. In addition, the base sequences corresponding to the amino acid sequences represented by SEQ ID No: 9 and SEQ ID No: 10 are preferably those represented by SEQ ID No: 11 and SEQ ID No: 12 respectively.

In one embodiment of the present invention, any plasmid can be used as the transformation plasmid as long as it contains a promoter unit, a secretory signal unit containing DNA encoding the secretory signal peptide represented by SEQ ID No: 1 or SEQ ID No: 2, and a target gene unit containing DNA encoding a protein useful for the diagnosis or treatment of an ischemic disease, functions to transform an anaerobic bacterium, and does not impair the anaerobic properties of the bacterium. However, when the gene transport carrier formed from the transformed anaerobic bacterium is used as a pharmaceutical, the risk of the transformation plasmid being horizontally transferred to another bacterium in the body such as for example *Escherichia coli*, the plasmid replicating in said other bacterium to which it has been horizontally transferred, and as a result the protein encoded by the plasmid being expressed in an unintended site cannot be ruled out. Therefore, in a preferred embodiment, the transformation plasmid is a non-shuttle plasmid.

In the present specification, a 'shuttle plasmid' means a plasmid that can replicate in two or more different types of hosts, and can be used interchangeably with a 'shuttle vector plasmid'. Therefore, the 'non-shuttle plasmid' means a plasmid that can replicate only in one type of host. That is, in the above embodiment, the transformation plasmid has a replication origin that functions only in an anaerobic bacterium as a transformation subject and does not have a replication origin that functions in a bacterium other than the above, and it is a plasmid that does not replicate in a bacterium other than a transformed anaerobic bacterium, such as *Escherichia coli*.

The transformation plasmid of the present invention may further contain another useful gene. Examples of said other useful gene include a selectable marker gene such as spectinomycin resistant gene (SPCM), a replication origin such as *Bifidobacterium* plasmid replication origin (pTB6), and a gene encoding a labeling protein such as GFP.

In a preferred embodiment, the transformation plasmid of the present invention is pFGF110 (SEQ ID No: 14) or pFGF111 (SEQ ID No: 15).

The transformation plasmid of the present invention may for example be prepared as follows.

For example, in accordance with a standard method, a shuttle plasmid may be prepared by inserting at least one type of promoter unit, secretory signal unit, and DNA encoding a protein useful for the diagnosis or treatment of a desired ischemic disease (target gene unit) into a shuttle plasmid having replication origins that function in a transformation bacterium and a bacterium other than the transformation bacterium, for example a *Bifidobacterium* and *Escherichia coli*.

If desired, a non-shuttle plasmid can be prepared by removing the replication origin for bacteria other than the transformed bacterium from this shuttle plasmid.

The procedure of each of the above steps may be carried out in accordance with methods known in the field of genetic engineering.

<Gene Transport Carrier>

In one aspect, the present invention relates to a gene transport carrier formed from an anaerobic bacterium transformed with the transformation plasmid of the present invention.

The gene transport carrier of the present invention is a gene transport carrier formed from the anaerobic bacterium transformed with the transformation plasmid of the present invention, can grow within tissue in an anaerobic environment, and can express and secrete a protein having targeted activity.

Since the gene transport carrier of the present invention specifically colonizes the site of an ischemic disease, the target protein is inevitably expressed and secreted specifically at the site of an ischemic disease. Therefore, the gene transport carrier of the present invention that can express a protein used for the diagnosis or treatment of an ischemic disease can diagnose or treat an ischemic disease effectively.

Since the gene transport carrier of the present invention specifically colonizes the site of an ischemic disease, it becomes possible by detecting the presence of the gene transport carrier to diagnose the site of an ischemic disease. Detection of the gene transport carrier may be carried out simply by for example labelling the gene transport carrier. From the viewpoint of use for the diagnosis of a disease, it is preferable that detection has low invasiveness and that there is little adverse effect on a living body due to labeling. Therefore, in a preferred embodiment of the present invention, the gene transport carrier expresses a fluorescence protein as a protein useful for diagnosis. Examples of the fluorescent protein include various types of green fluorescent protein (GFP) and red fluorescent protein (RFP).

Since it is assumed that the gene transport carrier of the present invention is administered into the body, it is necessary for the anaerobic bacterium used to have no toxicity or low toxicity. For example, even for a pathogenic bacterium such as *Clostridium* or *Salmonella*, one that has been made nonpathogenic may be used in the present invention. Therefore, in one embodiment of the present invention, the anaerobic bacterium of the present invention can be one formed by mutating a pathogenic bacterium so that it has low toxicity. However, since there is a possibility that a bacterium that has been mutated to have low toxicity can return to the original pathogenic bacterium by reverse mutation and exhibit toxicity, an inherently nonpathogenic bacterium is preferable. Therefore, in a preferred embodiment of the present invention, the anaerobic bacterium employs a nonpathogenic enterobacterium.

As the nonpathogenic enterobacterium that can be used in the present invention, a *Bifidobacterium* genus bacteria (*Bifidobacterium*) can preferably be cited. Examples of the *Bifidobacterium* include *Bifidobacterium adolescentis*, *Bifidobacterium angulatum*, *Bifidobacterium animalis*, *Bifidobacterium asteroides*, *Bifidobacterium bifidum*, *Bifidobacterium boum*, *Bifidobacterium breve*, *Bifidobacterium catenulatum*, *Bifidobacterium choerinum*, *Bifidobacterium coryneforme*, *Bifidobacterium cuniculi*, *Bifidobacterium denticolens*, *Bifidobacterium dentium*, *Bifidobacterium gallicum*, *Bifidobacterium gallinarum*, *Bifidobacterium globosum*, *Bifidobacterium indicum*, *Bifidobacterium infantis*, *Bifidobacterium inopinatum*, *Bifidobacterium lactis*, *Bifidobacterium lactentis*, *Bifidobacterium liberorum*, *Bifidobacterium longum*, *Bifidobacterium magnum*, *Bifidobacterium merycicum*, *Bifidobacterium minimum*, *Bifidobacterium mongoliens*, *Bifidobacterium parvulorum*, *Bifidobacterium pseudocatenulatum*, *Bifidobacterium pseudolongum*, *Bifidobacterium psychraerophilum*, *Bifidobacterium pullorum*, *Bifidobacterium ruminale*, *Bifidobacterium ruminantium*, *Bifidobacterium saeculare*, *Bifidobacterium scardovi*, *Bifidobacterium subtile*, *Bifidobacterium suis*, *Bifidobacterium thermacidophillum*, and *Bifidobacterium thermophilum*, and *Bifidobacterium longum* is most preferable.

All of these bacteria are either commercially available or easily available from a depository. For example, *Bifidobacterium longum* ATCC-15707, *Bifidobacterium bifidum* ATCC-11863, *Bifidobacterium infantis* ATCC-15697, etc. can easily be obtained from ATCC (The American Type Culture Collection).

Furthermore, the strain of each bacterium is not particularly limited; examples of strains of *Bifidobacterium longum* include *Bifidobacterium longum* 105-A strain, *Bifidobacterium longum* aE-194b strain, *Bifidobacterium longum* bs-601 strain, and *Bifidobacterium longum* M101-2 strain, and among them *Bifidobacterium longum* 105-A strain is preferable.

Examples of strains of *Bifidobacterium breve* include *Bifidobacterium breve* standard strain (JCM1192), *Bifidobacterium breve* aS-1 strain, and *Bifidobacterium breve* I-53-8W strain, and among them *Bifidobacterium breve* standard strain and *Bifidobacterium breve* aS-1 strain are preferable.

Examples of strains of *Bifidobacterium infantis* include *Bifidobacterium infantis* standard strain (JCM1222) and *Bifidobacterium infantis* I-10-5 strain, and among them *Bifidobacterium infantis* standard strain and *Bifidobacterium infantis* I-10-5 strain are preferable.

Furthermore, examples of strains of *Bifidobacterium lactentis* include *Bifidobacterium lactentis* standard strain (JCM1220).

The gene transport carrier of the present invention can be prepared by transforming any anaerobic bacterium that is to be transformed in accordance with a known method in the field of genetic engineering using the transformation plasmid of the present invention.

Preparation of the gene transport carrier of the present invention may be carried out in accordance with a method described in a commercial experimental book such as, for example, The Gene manual (Kodansha), Genetic Engineering Experimental Methods ed. By Y. Takagi (Kodansha), Molecular Cloning, Cold Spring Harbor Laboratory (1982), Molecular Cloning $2^{nd}$ Edition, Cold Spring Harbor Laboratory (1989), or Methods in Enzymology, 194 (1991).

<Pharmaceutical Composition>

In one aspect, the present invention relates to a pharmaceutical composition containing the gene transport carrier of the present invention.

The pharmaceutical composition of the present invention is not particularly limited as long as it contains the gene transport carrier of the present invention. With regard to the gene transport carrier of the present invention, at least one type thereof is contained, and two or more types may be contained. Furthermore, the pharmaceutical composition of the present invention may be used in a combination with an ischemic disease treatment agent or a pharmaceutical composition containing a compound, other than the gene transport carrier of the present invention, that exhibits an effect in treating an ischemic disease.

Moreover, the pharmaceutical composition of the present invention may contain an optional component in addition to the gene transport carrier of the present invention as long as it does not impair the effects of the present invention. Examples of such optional components include pharmacologically acceptable carriers, excipients, diluents, and agents for promoting the colonization and growth of the gene transport carrier. Examples of the agents for promoting colonization and growth include, but are not limited to, maltose, lactulose, arabinose, xylose, galactose, glucose, lactose, melibiose, melezitose, and raffinose, which are sugars that can be assimilated by the transformed bacterium used in the gene transport carrier of the present invention.

The dosage form of the pharmaceutical composition of the present invention is not particularly limited, and examples thereof include a liquid agent or a solid preparation containing the gene transport carrier of the present invention. The liquid agent may be produced by purifying a liquid culture of the anaerobic bacterium of the gene transport carrier of the present invention, adding thereto as necessary an appropriate physiological saline, supplementary fluid, or pharmaceutical additive, and charging an ampoule or a vial therewith. The solid preparation may be produced by adding an appropriate protecting agent to the liquid, charging an ampoule or a vial therewith, and then lyophilizing or L-drying it, or by adding an appropriate protecting agent to the liquid, lyophilizing or L-drying it, and then charging an ampoule or a vial therewith.

With regard to a method for administering the pharmaceutical composition of the present invention, both oral administration and parenteral administration are possible, but parenteral administration is preferable; for example, intravenous injection, subcutaneous injection, local infusion, intracerebroventricular administration, etc. may be carried out, and intravenous injection, that is, systemic administration, is most preferable.

The dose of the gene transport carrier of the pharmaceutical composition of the present invention is not particularly limited as long as it is an amount sufficient for it to grow at a disease site and for an effective therapeutic dose of active protein to be expressed, but from the viewpoint of economy and side effects being avoided wherever possible, it is preferable to use as small an amount as possible in a range that can give a necessary therapeutic effect.

The dose of the gene transport carrier in the pharmaceutical composition of the present invention may be selected as appropriate according to the extent of a disease and the body weight, age, and sex of the patient, and may be increased or decreased as appropriate according to the degree of improvement.

For example, when the pharmaceutical composition of the present invention is used, the dose is set appropriately according to the therapeutic activity for the disease exhibited by the anaerobic bacterium itself that is used, the type of protein, etc. having therapeutic activity for the disease produced by the anaerobic bacterium used, and the amount of the active protein produced by the anaerobic bacterium used.

Specifically, in the case of for example intravenous administration, since it is particularly necessary to suppress a risk such as embolization by a clump of bacteria, etc., it is preferable to inject an injectable preparation having as low a concentration as possible a plurality of times or to dilute it with an appropriate supplementary fluid and continuously infuse it. For example, in the case of an adult, $10^6$ to $10^{12}$ cfu of cells of the anaerobic bacterium of the present invention per kg of body weight is administered once or a plurality of times per day for one to a plurality of days continuously or at appropriate intervals. More specifically, 1 to 1000 mL per adult of a preparation containing $10^4$ to $10^{10}$ cfu/mL of cells of the *Bifidobacterium* of the present invention is administered directly or by diluting with an appropriate supplementary fluid once to multiple times per day continuously for one to several days.

Furthermore, in the case of local administration involving administration directly to the diseased tissue, since it is desirable that the bacterium colonizes and grows over the entire diseased tissue as much as possible, it is desirable that a high concentration injection is administered at a plurality of positions of the diseased tissue. For example, in the case of an adult, $10^6$ to $10^{12}$ cfu per kg of body weight of cells of the *Bifidobacterium* of the present invention are administered once to a plurality of times per day as necessary for one to a plurality of days continuously or at appropriate intervals. More specifically, 1 to 1000 mL per adult of a preparation containing $10^4$ to $10^{10}$ cfu/mL of cells of the *Bifidobacterium* of the present invention is administered directly a few times per day as necessary for one to several days continuously.

When it is confirmed that the bacterium in the diseased tissue has disappeared during the treatment period, the treatment is temporarily suspended, and the cells are administered in the same way as above.

The expression 'a combination of X and Y' in the present invention includes both a case in which X and Y are separate configurations and a case in which X and Y are of the same configuration (e.g. a mode containing X and Y). Furthermore, when X and Y are separate configurations, a case in which both X and Y further contain another component is also included.

The gene transport carrier of the present invention colonizes and grows specifically at the site of an ischemic disease, and does not grow in normal tissue that is not in an anaerobic environment. Therefore, the gene is delivered specifically to a disease site without there being local administration targeted at the site of an ischemic disease. Therefore, from the viewpoint of ease of administration, low invasiveness, etc., it is preferable for the pharmaceutical composition of the present invention to be administered systemically.

<Diagnostic Method or Therapeutic Method>

In one aspect, the present invention relates to a method for diagnosing or treating an ischemic disease, the method including administering any of the gene transport carriers described above.

Due to use of the gene transport carrier of the present invention, highly efficient and highly safe diagnosis or treatment becomes possible.

In the method of the present invention, the gene transport carrier of the present invention is administered to a subject having an ischemic disease. As an administration method, both oral administration and parenteral administration are possible, but parenteral administration is preferable; for example intravenous injection, subcutaneous injection, local infusion, intracerebroventricular administration, etc. can be carried out, and intravenous injection, that is, systemic administration, is most preferable.

Therefore, in a preferred embodiment of the method of the present invention, the gene transport carrier of the present invention is administered systemically. Since the gene transport carrier of the present invention can deliver the gene specifically to the site of an ischemic disease, even in a case of systemic administration such as intravenous injection it can exhibit the effects by colonizing and growing specifically at the site of the ischemic disease without being directly administered to an affected area using a catheter, intramuscular injection, etc. Therefore, a treatment with very low invasiveness is possible compared with conventional therapies.

EXAMPLES

The present invention is more specifically explained below by reference to Reference Examples and Examples, but the technical scope of the present invention is not limited to these Examples.

Example 1: Identification of Secretory Signal Peptide

Secretory signal peptides SP56 and SP67 were identified by the procedure below.

tinuing from the C terminal of each signal sequence, these being defined as a secretory signal unit. The sequences of the secretory signal units used are listed below. SP56 and a spacer peptide therefor (SEQ ID No: 9) and SP67 and a spacer peptide therefor (SEQ ID No: 10).

Example 2: Preparation of Various Types of hFGF2 Secretion Plasmids

PCR primers used for preparation of the plasmids are listed in Table 1.

TABLE 1

PCR Primers

| Name of primer | DNA sequence (5'-3') |
| --- | --- |
| Sp56-ins_F1 primer (SEQ ID No: 17) | CAAGAAGGATGCTTTATGAAAAAGAAGAAGACTATATCGGCTGC |
| SP56-ins_R1_FGF primer (SEQ ID No: 18) | GATCGAGCCGGCGGCATCGTTGATTTGCTGAATCTGACTTG |
| SP67-ins_P1 primer (SEQ ID No: 19) | CAAGAAGGATGCTTTATGAAGATAAACAATAAGGGCAAGG |
| SP67-ins_R1_FGF primer (SEQ ID No: 20) | GATCGAGCCGGCGGCGGGCTGGAACTTGGTGTATGTC |
| FGF1 primer (SEQ ID No: 21) | ACCATCATCATTGACCTTCTGCTCGTAGC |
| FGF2 primer (SEQ ID No: 22) | CGAGCCGGCGGCCATAAAGCATCCTTCTTGG |
| FGF3 primer (SEQ ID No: 23) | GTCAATGATGATGGTGGTGGTGCGACTTGGCGGACATCGGCAG |
| FGF4 primer (SEQ ID No: 24) | ATGGCCGCCGGCTCGATCAC |
| FGF35 primer (SEQ ID No: 25) | GCCGCCGGCTCGATCACCACCCTG |
| HuProm_R primer (SEQ ID No: 26) | AAAGCATCCTTCTTGGGTC |
| Hu SP26_F primer (SEQ ID No: 27) | CAAGAAGGATGCTTTATGAAGAAGAAAGCTCTTGCT |
| FGF_SP26L20_R primer (SEQ ID No: 28) | GATCGAGCCGGCGGCGTTCTGCGGTTCGGAGTTGTA |
| FGF-His_F primer (SEQ ID No: 29) | TGACCTTCTGCTCGTAGCGATTACTTCGAGCAT |
| FGF-His_R primer (SEQ ID No: 30) | ACGAGCAGAAGGTCACGACTTGGCGGACATCGGCAG |

The complete amino acid sequence of a *Bifidobacterium longum* NCC2705 strain-derived protein registered in the NCBI genome database (http://www.ncbi.nlm.nih.gov/genome/) was analyzed using the signal sequence prediction program SignalP 4.1 server (http://www.cbs.dtu.dk/services/SignalP/), which predicts the presence or absence of a secretory signal. The amino acid sequence of part of the protein for which the above analysis predicted that the N terminal of the protein had a secretory signal peptide sequence was subjected to topological analysis using the TMHMM Server v. 2.0 program (http://www.cbs.dtu.dk/services/TMHMM-2.0/), which estimates a transmembrane region (TM). Proteins for which this topological analysis result estimated that the N terminal of the protein had a TM were selected. These proteins were selected as *Bifidobacterium longum* NCC2705 strain-derived secretory signal peptides that were predicted to have a TM. In the amino acid sequence of the *Bifidobacterium longum* 105A strain corresponding to the amino acid sequences of the selected secretory signal peptides, part from the N terminal of the amino acid sequence of each protein to the amino acid sequence that had been estimated to be a protease cleavage site by the SignalP analysis was defined as the secretory signal peptide sequence (SP56 and SP67). Furthermore, the spacer peptide sequence was defined as the 20 amino acid residues con- 1. Preparation of Plasmid pFGF-Hu
(1) Preparation of Human FGF2-HisTag Insert Fragment (Insert Fragment 1)

Plasmid 'hFGF2 in pUC57' containing DNA encoding human FGF2 having a histidine tag fused to the C terminal thereof was acquired from GenScript. The DNA sequence of hFGF2 is an artificial DNA sequence (SEQ ID No: 31), for which the codon was optimized for *Bifidobacterium* based on the amino acid sequence of hFGF2 (an approximately 18 kDa protein with translation initiation from AUG of GenBank Accession No. #NM_002006). PCR amplification was carried out with 1 ng of plasmid hFGF2 in pUC57 as a template using a primer set of FGF4 primer (forward) and FGF3 primer (reverse). The primer sequences were designed so that 15 bp of the terminals of the insert fragment and the vector fragment overlapped one another. PCR amplification was carried out using a PrimeSTAR HS (Premix) kit (Takara Bio Inc.) with a concentration of 0.2 μM of each primer in a reaction volume of 50 μL. The amplification program employed one cycle of 10 sec at 98° C. (denaturation reaction), 5 sec at 55° C. (annealing reaction), and 30 sec at 72° C. (extension reaction); after 30 cycles were carried out extension was carried out at 72° C. for 30 sec, and an approximately 0.5 kbp hFGF2-HisTag insert fragment (insert fragment 1) was prepared.

(2) Preparation of Vector Fragment 1

PCR amplification was carried out in the same way as above using a primer set of FGF1 primer (forward) and FGF2 primer (reverse) with 1 ng of plasmid pCDshuttle (International Patent Application WO2009/128272) (SEQ ID No: 32) as a template. The PCR extension reaction was at 72° C. for 4 minutes. The length of vector fragment 1 was about 3.9 kbp.

(3) In-Fusion Reaction

Insert fragment 1 and vector fragment 1 prepared above were ligated using an In-Fusion (registered trademark) HD Cloning kit (Takara Bio Inc.). That is, 50 ng of the vector fragment and 13 ng of the insert fragment were added to a microtube, 2 µL of 5× In-Fusion HD Enzyme premix and 1 µL of Cloning Enhancer from the kit were further added thereto, and the reaction solution volume was adjusted to 10 µL using 0.1×TE buffer (1 mM Tris-HCl, 0.1 mM EDTA, pH 7.5). This was incubated at 37° C. for 15 minutes and further incubated at 50° C. for 15 minutes. The procedure was otherwise in accordance with the product instructions of the kit, and In-Fusion reaction solution 1 was thus prepared.

(4) Transformation of *Escherichia coli* and Confirmation of DNA Sequence of Plasmid pFGF-Hu Transformation of *Escherichia coli* TOP10 competent cells (Invitrogen) was carried out in accordance with the product instructions using the In-Fusion reaction solution 1 above. The cell suspension after transformation was spread on a 75 µg/mL spectinomycin-containing LB agar medium and cultured at 37° C. overnight. *Escherichia coli* colonies formed on the agar medium were subjected to shaking culture in 75 µg/mL spectinomycin-containing LB liquid medium at 37° C. overnight, and a plasmid was extracted therefrom using a QIAprep Spin Miniprep kit (Qiagen). In order to determine the sequence for a region containing the human FGF2 expression cassette (5'-Hu promoter-human FGF2 protein-His tag-Hu terminator-3') of the extracted plasmid, sequencing was carried out using a Big Dye (registered trademark) Terminator v3.1 Cycle Sequencing kit (Applied Biosystems, Inc.). The extracted plasmid was named pFGF-Hu.

2. Preparation of Plasmids pHuSP56L20-FGF2 and pHuSP67L20-FGF2

(1) Preparation of SP56L20 and SP67L20 Insert Fragments (Insert Fragments 2 and 3)

PCR amplification was carried out using the primer set of SP56-ins_F1 primer (forward) and SP56-ins_R1 FGF primer (reverse) described in Table 1 with the genome DNA of the *Bifidobacterium longum* 105-A strain as a template. The primer sequence was designed so that 15 bp terminals of the insert fragment and the vector fragment overlapped one another. PCR amplification was carried out using a PrimeSTAR HS (Premix) kit (Takara Bio Inc.) with 0.2 µM concentration of each primer in a reaction volume of 20 µL. The amplification program employed one cycle of 10 sec at 98° C., 5 sec at 65° C., and 20 sec at 72° C., after 30 cycles were carried out extension was carried out at 72° C. for 30 sec, and an approximately 0.2 kbp SP56L20 insert fragment amplification product (insert fragment 2) was prepared.

An SP67L20 insert fragment (insert fragment 3) was prepared in the same way as above except that SP67-ins_F1 primer (forward) and SP67-ins_R1_FGF primer were used as PCR amplification primers.

(2) Preparation of Vector Fragment 2 Containing DNA Encoding Human FGF2 Protein

PCR amplification was carried out by the same method as in the preparation of the above insert fragment using the primer set of FGF35 primer (forward) and HuProm_R primer (reverse) described in Table 1 with plasmid pFGF-Hu as a template. The reaction volume in PCR was 50 µL. The amplification program employed one cycle of 10 sec at 98° C., 5 sec at 65° C., and 4 min 30 sec at 72° C.; after 30 cycles were carried out, extension was carried out at 72° C. for 30 sec, and an approximately 4.3 kbp vector fragment amplification product was prepared. This PCR product was subjected to electrophoresis using 0.8% agarose gel (containing ethidium bromide), and a gel containing an approximately 4.3 kbp DNA band was cut out while irradiating with UV. DNA was extracted from this gel using a QIAquick Gel Extraction Kit (Qiagen) and defined as vector fragment 2 (straight chain pHu-FGF2 fragment, SEQ ID No: 33).

(3) In-Fusion Reaction

Insert fragment 2 or insert fragment 3 and vector fragment 2 prepared above were ligated using an In-Fusion (registered trademark) HD Cloning kit (Takara Bio Inc.). That is, 68 ng of the vector fragment amplification product and 6.15 ng (in the case of insert fragment 2) or 6.55 ng (in the case of insert fragment 3) of the insert fragment amplification product were added to a microtube, 2 µL of 5× In-Fusion HD Enzyme premix and 1 µL of Cloning Enhancer of the kit were further added thereto, and the reaction solution volume was adjusted to 10 µL using 0.1×TE buffer (1 mM Tris-HCl, 0.1 mM EDTA, pH 7.5). This was incubated at 37° C. for 15 minutes and then further incubated at 50° C. for 15 minutes. The procedure was otherwise in accordance with the product instructions of the kit, and In-Fusion reaction solution 2 was thus prepared.

(4) Confirmation of DNA Sequences of *Escherichia coli* Transformant 1 and Plasmids pHuSP56L20-FGF2 and pHuSP67L20-FGF2

Transformation of *Escherichia coli* HST16CR competent cells (Takara Bio Inc.) was carried out in accordance with the product instructions using In-Fusion reaction solution 2 above. The cell suspension after transformation was spread on 75 µg/mL spectinomycin-containing LB agar medium, and cultured at 37° C. overnight. *Escherichia coli* colonies formed on the agar medium were subjected to shaking culture in 75 µg/mL spectinomycin-containing LB liquid medium at 37° C. overnight, and a plasmid was extracted therefrom using a QIAprep Spin Miniprep kit (Qiagen). Sequencing of a region containing the human FGF2 secretion expression cassette (5'-Hu promoter-SP56L20-human FGF2 protein-His tag-Hu terminator-3') or (5'-Hu promoter-SP67L20-human FGF2 protein-His tag-Hu terminator-3') in the extracted plasmid was carried out in the same way as in 1. (4) above. The extracted plasmids were named pHuSP56L20-FGF2 and pHuSP67L20-FGF2 respectively. The sequences of regions containing the human FGF2 secretion expression cassette of each plasmid are shown in SEQ ID Nos: 34 and 35 respectively.

3. Preparation of Plasmid pHuSP26L20-FGF2-dHis (1) Preparation of SP26L20 Insert Fragment (Insert Fragment 4)

PCR amplification was carried out in the same way as in 2. (1) above using a primer set of Hu_SP26_F primer (forward) and FGF_SP26_L20_R primer (reverse) with 80 ng of the genome DNA of *Bifidobacterium longum* 105A as a template. PCR extension was carried out at 72° C. for 14 sec, and the PCR solution volume was 20 µL. The length of the insert fragment was about 0.1 kbp.

(2) In-Fusion Reaction

In-Fusion reaction solution 3 was prepared by carrying out an In-Fusion reaction in the same way as in 2. (3) above using insert fragment 4 and vector fragment 2 prepared above. The amount of vector used in the In-fusion reaction was 50 ng, and the amount of insert was 4.2 ng.

(3) Transformation 2 of *Escherichia coli* and Confirmation of DNA Sequence of Plasmid pHuSP26L20-FGF2

Transformation of *Escherichia coli* TOP10 competent cells, extraction of DNA from recombinant *Escherichia coli*, and determination of the sequence of the human FGF2 expression cassette-containing region (5'-Hu promoter-SP26L20-human FGF2 protein-His tag-Hu terminator-3') were carried out by the same method as in 1. (4) above using In-Fusion reaction solution 3. The extracted plasmid was named pHuSP26L20-FGF2.

(4) Preparation of Human FGF2 Insert Fragment (Insert Fragment 5)

PCR amplification was carried out in the same way as 2. (1) above using a primer set of FGF35 primer (forward) and FGF-His_R primer (reverse) with 1 ng of plasmid pHuSP26L20-FGF2 as a template. The PCR annealing temperature was 60° C., and extension was at 72° C. for 35 sec. The length of the insert fragment was about 0.5 kbp.

(5) Preparation of Vector Fragment 3

PCR amplification was carried out in the same way as in 2. (2) above using a primer set of FGF-His_F primer (forward) and FGF_SP26_L20_R primer (reverse) with 1 ng of plasmid pHuSP26L20-FGF2 as a template. The PCR annealing temperature was 60° C., and extension was at 72° C. for 4 min 10 sec. The vector fragment length was about 4 kbp.

(6) In-Fusion Reaction

In-Fusion reaction solution 4 was prepared by carrying out an In-Fusion reaction in the same way as in 2. (3) above using insert fragment 5 and vector fragment 3 prepared above. The amount of vector used in the In-fusion reaction was 20 ng, and the amount of insert was 4 ng.

(7) Transformation 3 of *Escherichia coli* and Confirmation of Sequence of Plasmid pHuSP26L20-FGF2-dHis Transformation of *Escherichia coli* and DNA extraction of the recombinant *Escherichia coli* were carried out by the same method as in 2. (4) above using In-Fusion reaction solution 4. Determination of the sequence of the human FGF2 expression cassette-containing region (5'-Hu promoter-SP26L20-human FGF2 protein-Hu terminator-3') was carried out using the extracted DNA. The extracted plasmid was named pHuSP26L20-FGF2-dHis.

4. Preparation of Plasmids pHuSP56L20-FGF2-dHis and pHuSP67L20-FGF2-dHis (1) Preparation of Vector Fragment 4 Containing DNA Encoding Human FGF2 Protein Vector fragment 4 (straight chain pHuSP26L20-FGF2-dHis fragment, SEQ ID No: 36) was prepared by carrying out PCR by the same method as in 2. (2) above except that plasmid pHuSP26L20-FGF2-dHis was used as a template.

(2) In-Fusion Reaction

In-Fusion reaction solution 5 was prepared by carrying out the same method as in 2. (3) above using insert fragment 2 or 3 (SP56 or SP67) and vector fragment 4 prepared above. The amount of vector was 75 ng.

(3) Transformation 4 of *Escherichia coli* and Confirmation of DNA Sequences of Plasmids pHuSP56L20-FGF2-dHis and pHuSP67L20-FGF2-dHis Transformation of *Escherichia coli* HST16CR competent cells and plasmid extraction from recombinant *Escherichia coli* were carried out by the same procedure as in 2. (4) above using In-Fusion reaction solution 5. Determination of the complete sequence of the extracted plasmid was carried out by the same procedure. The extracted plasmids were named pHuSP56L20-FGF2-dHis and pHuSP67L20-FGF2-dHis.

5. Preparation of Plasmids pFGF110 and pFGF111

(1) Removal of pUCori from Plasmid pHuSP56L20-FGF2-dHis and pHuSP67L20-FGF2-dHis 3 µg of plasmid pHuSP56L20-FGF2-dHis or pHuSP67L20-FGF2-dHis was digested with restriction enzyme BamHI (Thermo Scientific) and Bgl II (Thermo Scientific) and cleaved into two fragments, that is, an approximately 0.7 kbp pUC ori-containing DNA fragment and the other portion (about 3.8 kbp). This reaction solution was subjected to electrophoresis using 0.8% agarose gel (containing ethidium bromide), and a gel containing an approximately 3.8 kbp DNA band was cut out while irradiating with UV. DNA was extracted from this gel using a QIAquick Gel Extraction Kit (Qiagen) to give straight chain non-shuttle plasmids pFGF110 and pFGF111.

(2) Preparation of Non-Shuttle Plasmids pFGF110 and pFGF111

Self ligation of the straight chain non-shuttle plasmids was carried out as follows using a Rapid DNA Ligation Kit (Thermo Scientific). That is, 80 µL of 5× Rapid Ligation Buffer and 8 µL of T4 DNA Ligase included in the kit were added to 400 ng of the straight chain non-shuttle plasmid, and it was made up to 400 µL with 0.1×TE. 80 µL thereof was dispensed into each of five microtubes, and a self ligation reaction was carried out at 22° C. for 5 min. These reaction solutions were combined, subjected to a Proteinase K treatment, then removal of protein with phenol/chloroform, chloroform extraction, and alcohol precipitation by standard methods. DNA that had been precipitated with alcohol was dissolved in 0.1×TE, thus giving non-shuttle plasmids pFGF110 (SEQ ID No: 14) and pFGF111 (SEQ ID No: 15).

Example 3: Preparation of Recombinant *Bifidobacterium*

(1) Preparation of FGF110 Strain and FGF111 Strain

Transformation of the *Bifidobacterium longum* 105-A strain was carried out by an electroporation system (Genepulser II, Bio-Rad) using the non-shuttle plasmid pFGF110 and pFGF111 DNA solutions prepared above. After electric shock (2 kV, 25 µF, 200Ω), a mixed liquid of 800 µL of IMR liquid medium and 50 µL of vitamin C-containing liquid (a solution containing 35 g of ascorbic acid, 2 g of L-cysteine hydrochloride monohydrate, and 11 g of sodium carbonate per 100 mL) was immediately added to the cuvette (2 mm gap), and this was collected in a 2 mL sterile microtube. The cap of this 2 mL tube was loosened and the tube was placed in a sealed container together with an oxygen-absorbing and carbon dioxide-generating agent (AnaeroPack (registered trademark) Kenki, Mitsubishi Gas Chemical Company, Inc.) and incubated in an incubator at 37° C. for 3 hours.

Each cell suspension after incubation was spreadon 75 µg/mL spectinomycin-containing IMR agar medium. These plates were placed in a sealed container together with the oxygen-absorbing and carbon dioxide-generating agent and cultured in an incubator at 37° C. for 2 days.

Among colonies formed on the spectinomycin-containing IMR agar medium, the transformant with plasmid pFGF110 was defined as *Bifidobacterium longum* 105-A/pFGF110 strain (hereinafter called FGF110 strain) and the transformant with plasmid pFGF111 was defined as *Bifidobacterium longum* 105-A/pFGF111 strain (hereinafter called FGF111 strain).

(2) Preparation of SP56 Strain and SP67 Strain

Transformation of the *Bifidobacterium longum* 105-A strain was carried out by the same method as in (1) above using shuttle plasmids pHuSP56L20-FGF2 and pHuSP67L20-FGF2, thus giving *Bifidobacterium longum* 105-A/pHuSP56L20-FGF2 strain (hereinafter called SP56 strain) and *Bifidobacterium longum* 105-A/pHuSP67L20-FGF2 strain (hereinafter called SP67 strain).

(3) Preparation of Negative Control Strain

Transformation of *Bifidobacterium longum* 105-A strain was carried out by the same method as above (preparation of FGF110 strain and FGF111 strain) using pBEshuttle (SEQ ID No: 37), which is a vector backbone, described in WO2011/093467 thus giving *Bifidobacterium longum* 105-A/pBEshuttle strain (hereinafter called BEshuttle strain).

Example 4: Analysis of Expressed Protein (1) Culturing of Recombinant *Bifidobacterium*

10 mL of MRS (Beckton Dickinson) liquid medium having added thereto 100 μL of a vitamin C-containing liquid and spectinomycin (final concentration 75 μg/mL) was inoculated with the FGF110 strain, the FGF111 strain, and *Bifidobacterium longum* 105A/pFGF12a strain (hereinafter called FGF12a strain) described in Patent Document 7 (WO2013/008881), and anaerobic culturing was carried out at 37° C. for 24 hours, thus giving activated culture broth. Subsequently, 100 μL of a vitamin C-containing liquid and spectinomycin at 75 μg/mL were added to mL of a medium containing DMEM (Cat No. 11885-084: Life Technologies Corporation):MRS at a ratio of 9:1, thus carrying out inoculation with 100 μL of the activated culture broth. This was anaerobically cultured at 37° C. for 15 hours.

(2) Preparation of Sample

The supernatant of the recombinant *Bifidobacterium* culture was subjected to precipitation with trichloroacetic acid (TCA) by a standard method, and redissolved in 1×SDS sample buffer. This was thermally treated at 95° C. for 3 min and subjected to western analysis.

(3) Western Blotting

Each culture supernatant concentrate (corresponding to 0.2 mL of culture supernatant) and recombinant human FGF2 (Peprotech, molecular weight 17.2 kDa) as a positive control were subjected to electrophoresis using Mini-protean (registered trademark) TGX™ gel (4 to 20%) (Bio-rad), and the gel was transferred to a PVDF membrane (iBlot Transfer Stacks, Life Technologies Corporation) using an iBlot transfer device (Life Technologies Corporation). The PVDF membrane after completion of blotting was blocked (2% ECL Prime Blocking agent (GE Healthcare Japan) in TTBS). Anti FGF-2 human rabbit poly (H-131, Santa Cruz Biotechnology Inc.) was added as a primary antibody, and shaking was carried out at 4° C. overnight. After the primary antibody reaction, the membrane was washed with TTBS for about 5 min, this was repeated six times, Goat anti-rabbit IgG HRP (Santa Cruz Biotechnology Inc.) was added as a secondary antibody, and shaking was carried out at room temperature for 1 hour. The membrane after completion of the antibody reaction was illuminated using Western Lightning Ultra (Perkin Elmer). Analysis was carried out using an imaging device (Fluor-S MAX, Bio-rad).

(4) Results

Figure 5:
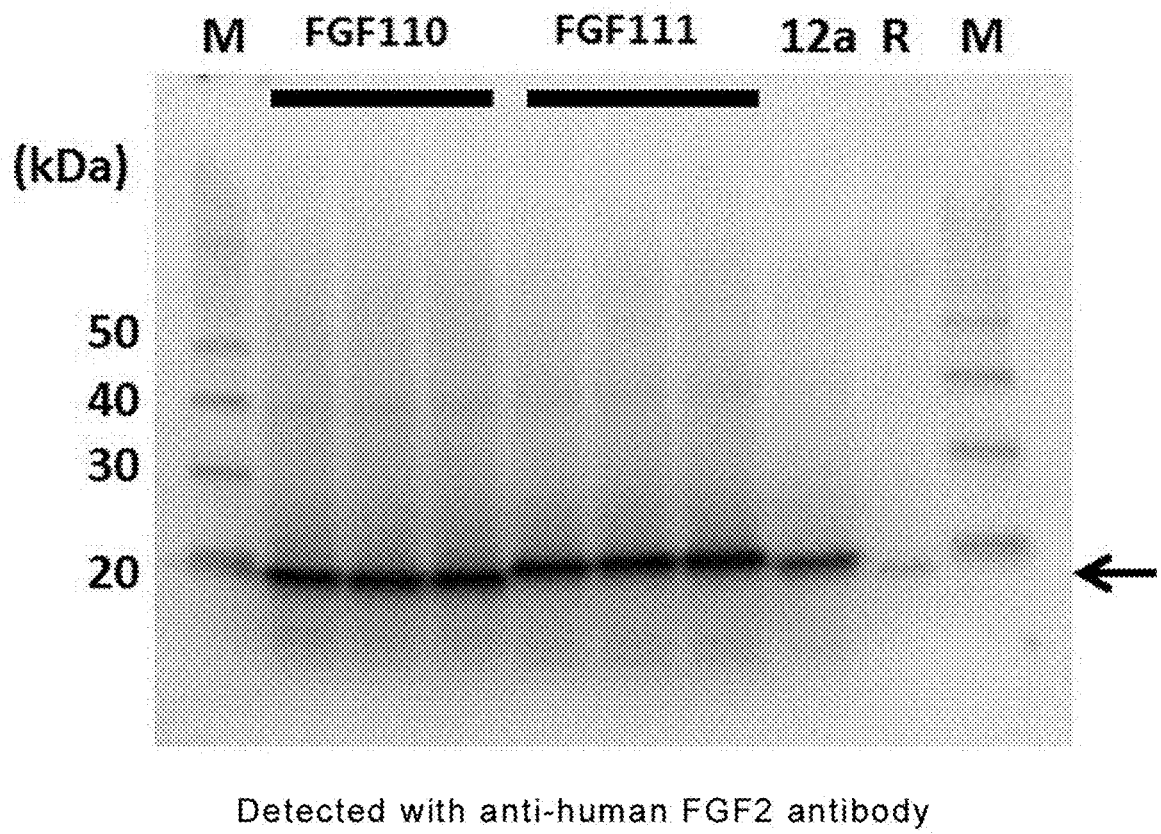
FIG. 5 shows the result of western blotting of FGF110 strain and FGF111 strain culture supernatants. M: molecular weight marker, FGF110: FGF110 strain culture supernatant concentrate, FGF111: FGF111 strain culture supernatant concentrate, 12a: FGF12a strain culture supernatant concentrate, R: recombinant human FGF2. It is confirmed that FGF110 strain, FGF111 strain, and FGF12a strain have a band at the same position as that of the recombinant (molecular weight about 17 kDa), which is a positive control.

The results are shown in FIG. 5. For the FGF110 strain and the FGF111 strain, a band was confirmed at a predicted molecular weight of about 20 kDa.

Example 5: Measurement of Biological Activity of His-Tag Purified FGF2 from *Bifidobacterium*

(1) Purification of Human FGF2 from Culture Supernatant of SP56 Strain and SP67 Strain Culturing of the SP56 strain and the SP67 strain was carried out by the same method as in Example 4 above. The culture broth was centrifuged, the supernatant was collected, and ammonium sulfate precipitation was carried out by a standard method. Furthermore, affinity purification was carried out using a purification kit for a protein having a histidine tag (TALON (registered trademark) Metal Affinity Resin, Takara Bio Inc.). After affinity purification, the buffer was replaced with PBS using an ultrafiltration cassette (Amicon Ultra-4, 10K, Millipore), thus giving a purified human FGF2 solution. The amount of human FGF2 in the purified solution was measured using a Quantikine ELISA FGF2 basic Immunoassay (R&D Systems; DFB50).

(2) Growth Promoting Activity of FGF2 Protein in SP56 Strain and SP67 Strain Secretion The biological activity of FGF2 was evaluated in activity in promoting cell proliferation of human FGF2 purified from the culture supernatant of the SP56 strain and the SP67 strain as described above by adding to NIH/3T3 cells (cell line for mouse fibroblast). That is, NIH/3T3 cells were cultured in DMEM medium (10% (v/v)FBS) at 37° C. under conditions of 5% $CO_2$, $1 \times 10^3$ cells were plated on each well of a 96-well plate with DMEM medium (5% (v/v)FBS), and cultured at 37° C. under conditions of 5% $CO_2$ for 24 hours. Subsequently, replacement was carried out with a medium formed by mixing purified human FGF2 derived from the SP56 strain and the SP67 strain or recombinant hFGF2 (R&D systems) with DMEM medium (5% (v/v)FBS) so that the FGF2 concentration was 0.25 ng/mL to 10 ng/mL. As a negative control, replacement with a medium that was mixed with PBS(−) instead of the FGF2 solution was also carried out in the same manner. These plates were cultured at 37° C. under conditions of 5% $CO_2$ for 4 days.

100 μL of Cell Counting kit-8 (Dojindo) was added to the plate, incubation was then carried out at 37° C. under conditions of 5% $CO_2$ for a further 2 hours, and the activity in promoting cell proliferation for the NIH/3T3 cells was measured by measuring the absorbance at wavelengths of 450 nm and 630 nm (reference wavelength).

(3) Results

Figure 6:
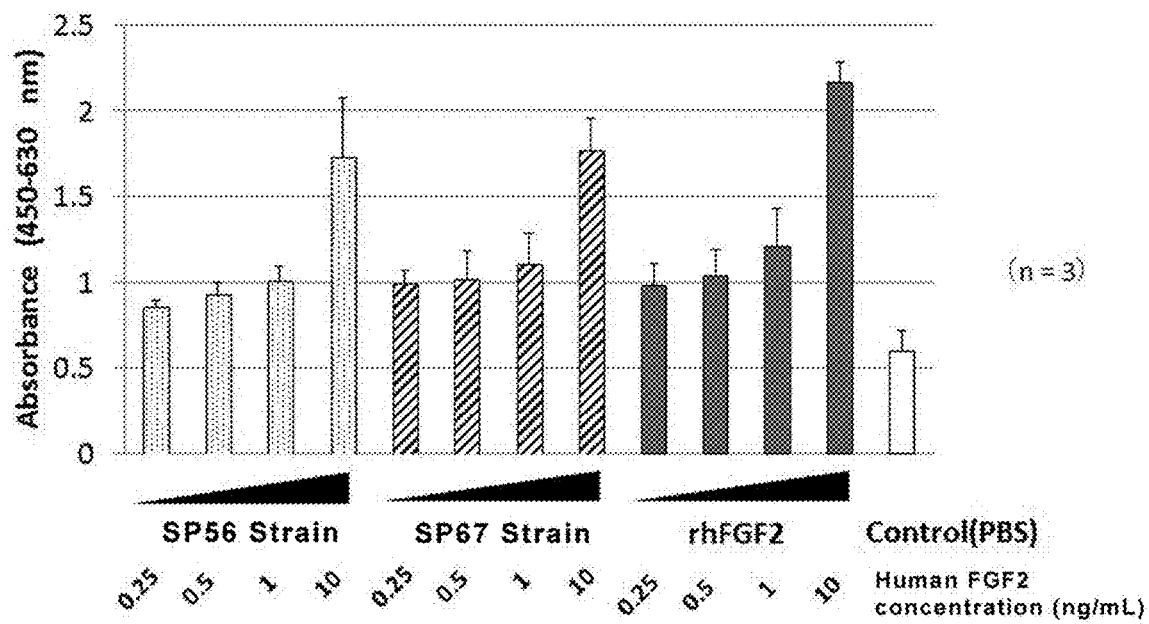
FIG. 6 shows NIH/3T3 cell proliferation promoting activity of human FGF2 protein secreted by SP56 strain and SP67 strain. Ordinate: absorbance at 450-630 nm, abscissa: human FGF2 concentration (ng/mL). Human FGF2 secreted by the SP56 and SP67 strains has concentration-dependent cell proliferation promoting activity in the same way as rhFGF2.

The results are shown in FIG. 6.

Human FGF2 secreted by the SP56 and SP67 strains had concentration-dependent activity in promoting cell proliferation.

Example 6: Comparison of Stability of Amount of FGF2 Secreted (1) Method 10 mL of MRS (containing 75 μg/mL spectinomycin and 1% vitamin C-containing liquid) medium was inoculated at 1% with a glycerol stock of *Bifidobacterium longum* 105A/pFGF12a strain described in WO2013/008881, the FGF110 strain, and the FGF110 strain, and anaerobically cultured at 37° C. for 24 hours, thus giving an activated culture broth. Subsequently, the same medium was inoculated with the activated culture at 1%, and cultured in the same manner for 24 hours, thus giving a passage culture broth. Following this, the same passage was repeated every 24 hours.

The day before measuring the amount of human FGF2 secreted, DMEM:MRS (9:1) (containing 75 µg/mL spectinomycin and 1% vitamin C-containing liquid) medium, which is a medium for human FGF2 measurement, was inoculated with the passage culture broth at 0.5% and cultured at 37° C. for 13 hours. Measurement of the amount of human FGF2 secreted was carried out on the $2^{nd}$ day, the $4^{th}$ day, and the $7^{th}$ day after culturing from the glycerol stock.

A culture supernatant was obtained by centrifuging the culture broth in the medium for human FGF2 measurement. The amount of FGF2 protein in this culture supernatant was measured using a Quantikine ELISA FGF2 basic Immunoassay (R&D Systems; DFB50).

(2) Results

Figure 7:
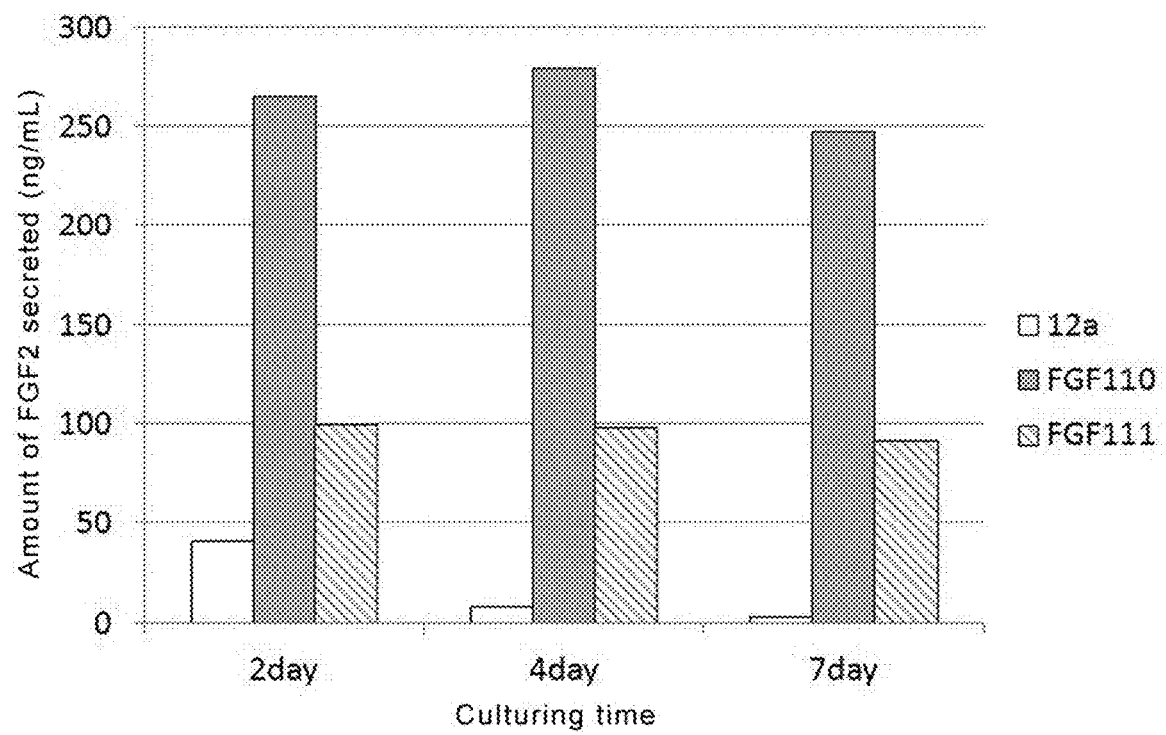
FIG. 7 shows change in amount of human FGF2 secreted when carrying out long-term culturing. Ordinate: amount of FGF2 secreted (ng/mL), abscissa: culturing time. At any point of time at 2 days, 4 days, or 7 days, the amount of FGF2 secreted is, in order from the highest, the FGF110 strain, the FGF111 strain, and the FGF12a strain. The amount of FGF2 secreted by the FGF12a strain decreases greatly from the 4th day of culturing onward, but for the FGF110 strain and the FGF111 strain stable expression/secretion is observed up to the end.

The results are shown in FIG. 7.

The amount of FGF2 secreted was, in order from the highest, shown by the FGF110 strain, the FGF111 strain, and the FGF12a strain.

The amount of FGF2 secreted by the FGF12a strain decreased greatly from 4th day of culturing onward.

Example 7: Change of Blood Flow in Affected Limb of Chronic Ischemia Model Mouse Treated with FGF110 Strain In order to check the therapeutic effect of the gene transport carrier of the present invention at the site of an ischemic disease, a mouse model with lower limb ischemia was prepared and examined by administering the human FGF2 secreting *Bifidobacterium*.

(1) Preparation of Mouse Lower Limb Ischemia Model (Necrotic Model)

As a test animal, a 19 week old female BALB/c mouse (Japan SLC, Inc.) was used. As anesthesia, Somnopentyl (Kyoritsu Seiyaku) was diluted to 2.5 mg/mL and intraperitoneally injected at 0.4 mL per 20 g of body weight. At the same time as anesthesia 0.2 mL of heparin sodium (Nipro) (diluted to 50 u/mL with physiological saline) was intraperitoneally injected. After hair was removed from the abdomen to the lower limb, the femoral artery was ligated with 9-0 polypropylene thread, and the femoral artery center was excised. The interior of the wound was cleaned with physiological saline, and the wound was sutured with 6-0 nylon thread. Postoperative rewarming was carried out, and 0.2 mL of heparin was subcutaneously injected. Also on the $1^{st}$ and $2^{nd}$ day after the operation, 0.4 mL of heparin was subcutaneously injected.

On the $6^{th}$ day after the first operation, anesthesia was carried out in the same manner as for the first time, and after administration of heparin the femoral artery periphery was ligated and excised. Administration of heparin was carried out in the same manner as for the first time up to the $2^{nd}$ day after the operation. Furthermore, 1 mL of 10% maltose was intraperitoneally administered every day after administration of the recombinant *Bifidobacterium*.

(2) Measurement of Blood Flow by Laser Doppler Blood Flow Meter

After the mouse was anesthetized, measurement of blood flow was carried out using a laser Doppler blood flow meter (Moor Instruments). Blood flow was measured quantitatively for both sides from below the tarsocrural joint to the toe, and was expressed as a ischemic side/non-ischemic side ratio. Measurement of blood flow was carried out on days 2, 7, 14, 21, and 36, with the second operation as day 0.

(3) Administration of Recombinant *Bifidobacterium*

Frozen preparation of the FGF110 strain, which is a human FGF2 secreting *Bifidobacterium* was used after adjusting the bacterial concentration by adding PBS. 0.6× $10^9$ cfu was administered twice a day from the tail vain on days 3, 4, 11, 18, 25, and 32 with the second operation on the lower limb ischemia model as day 0. As control groups, a group for which the frozen preparation of the BEshuttle strain was administered in the same amount and a group for which PBS was administered in the same volume (0.2 mL) were set.

(4) Results

Figure 8:
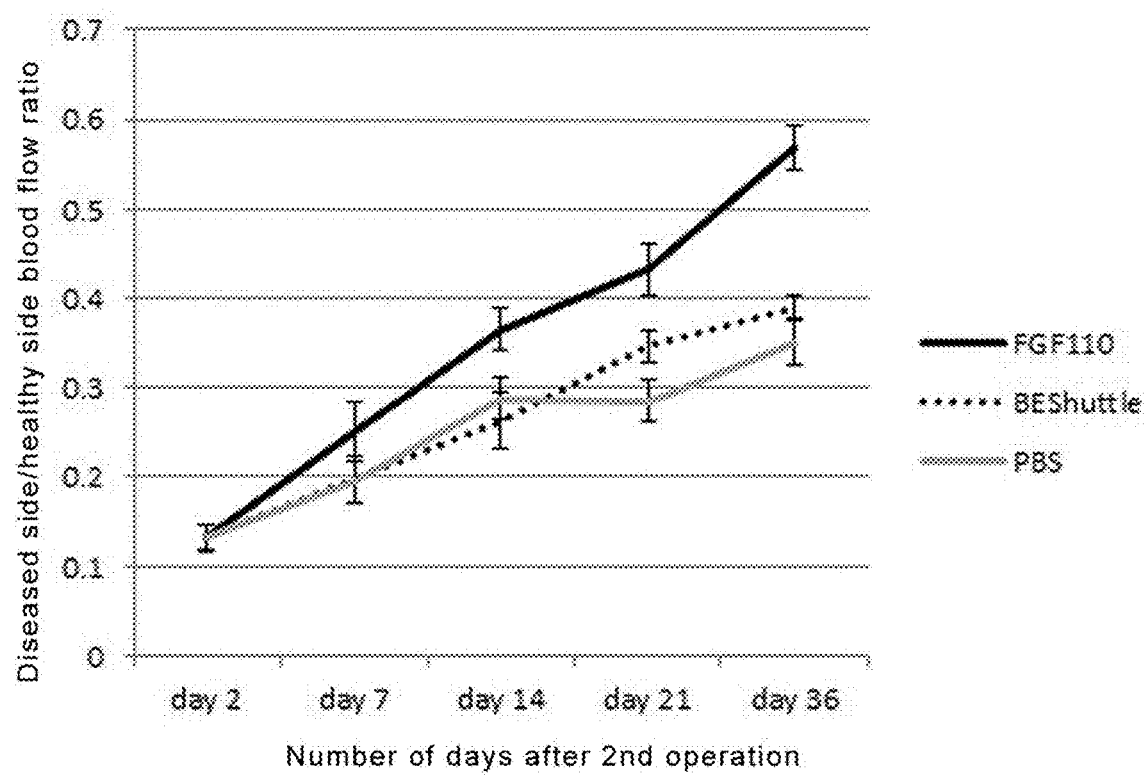
FIG. 8 shows the effect of FGF110 in improving blood flow. Ordinate: ischemic side/non ischemic side blood flow ratio, abscissa: number of days after $2^{nd}$ operation. The FGF110 treated group shows a significant effect in improving blood flow compared with PBS and BEshuttle groups from day 14 onward. This effect continues up to day 36.

The FGF110 treated group showed a significant blood flow improvement effect from day 14 onward compared with the PBS and BEshuttle groups. The effect was sustained up to day 36 (Table 2, FIG. 8).

TABLE 2

Effect of FGF110 in improving blood flow

| Day | FGF110 (n = 10) | BEshuttle (n = 10) | PBS (n =10) |
| --- | --- | --- | --- |
| day 2 | 0.132 ± 0.013 | 0.131 ± 0.015 | 0.132 ± 0.015 |
| day 7 | 0.251 ± 0.033 | 0.197 ± 0.025 | 0.195 ± 0.023 |
| day 14 | 0365 ± 0.024 | 0.263 ± 0.031 | 0.288 ± 0.023 |
| day 21 | 0.432 ± 0.030 | 0.347 ± 0.018 | 0.285 ± 0.023 |
| day 36 | 0.568 ± 0.024 | 0.389 ± 0.014 | 0.351 ± 0.026 |

Example 8: Plasmid Retention Stability after Passage Culturing in Nonselective Medium (1) Method In addition to the FGF110 strain and the FGF111 strain prepared above, a glycerol stock of the BEshuttle strain as a negative control strain was inoculated at 1% into 5 mL of MRS (containing 75 µg/mL spectinomycin and 1% vitamin C-containing liquid) medium, and anaerobically cultured at 37° C. for 24 hours, thus giving an activated culture broth. The same medium was inoculated with the activated culture broth at 1%, and cultured in the same manner for 24 hours, thus giving a pre-culture broth. Subsequently, each strain was inoculated into 5 mL of MRS (containing 1% vitamin C-containing liquid) medium, which is a nonselective medium not containing spectinomycin, and passaged to the same culture broth every 24 hours, passage culturing being thus repeated with the nonselective medium. The culture broth that had been passaged seven times was diluted as appropriate with an anaerobic diluent, this was spread on BL agar medium, and anaerobic culturing was carried out at 37° C. for 2 days.

100 colonies were randomly selected from the colonies formed on the BL agar medium, and BL-bS and BL agar media were punctured with these colonies and anaerobically cultured at 37° C. for 1 day. Growth of the *Bifidobacterium* on the puncture mark on each medium was confirmed, and (number of growth positions on BL-bS agar medium)/(number of growth positions on BL agar medium)×100 was calculated, thus giving a plasmid-retaining bacteria percentage.

(2) Results

The results are shown in Table 3. From the result of measuring plasmid retention stability, both the FGF110 strain and the FGF111 strain showed a very high percentage of plasmid-retaining bacteria.

TABLE 3

Plasmid retention stability

| Name of strain | Plasmid-retaintng bacteria percentage (%) |
| --- | --- |
| FGF110 | 97 |
| FGF111 | 100 |
| BEshuttle | 99 |

INDUSTRIAL APPLICABILITY

In accordance with the transformation plasmid of the present invention, a transformation plasmid for transforming an anaerobic bacterium can be provided, the transformation plasmid enabling a target protein to be expressed and secreted highly and stably. Therefore, compared with conventional methods an angiogenic therapy can be carried out simply with low invasiveness and high efficiency. Furthermore, since an anaerobic bacterium itself transformed with such a plasmid becomes a gene transport carrier, the efficiency with which a gene is introduced into a target site is not an issue, and a very highly efficient treatment can be carried out compared with conventional methods. This enables a subject such as an elderly person for whom angiogenic therapy should be effective but could not be applied due to problems with high invasiveness and systemic side effects to be treated effectively.

The invention claimed is:

1. A transformation plasmid for an anaerobic bacterium, wherein the transformation plasmid consists of the base sequence of pFGF110 (SEQ ID NO: 14) or pFGF111 (SEQ ID NO: 15).

2. A gene transport carrier comprising an anaerobic bacterium transformed with the transformation plasmid according to claim 1.

3. The gene transport carrier according to claim 2, wherein the anaerobic bacterium is a *Bifidobacterium*.

4. The gene transport carrier according to claim 3, wherein the *Bifidobacterium* is a *Bifidobacterium longum*.

5. A pharmaceutical composition comprising the gene transport carrier according to claim 2.

6. The pharmaceutical composition according to claim 5, wherein the pharmaceutical composition further comprises an agent for promoting colonization and growth of the gene transport carrier at the site of an ischemic disease.

7. The pharmaceutical composition according to claim 6, wherein the agent for promoting colonization and growth is at least one type selected from the group consisting of maltose, lactulose, arabinose, xylose, galactose, glucose, lactose, melibiose, melezitose, and raffinose.

8. A method for treating an ischemic disease, the method comprising administering the gene transport carrier according to claim 2.

9. The method according to claim 8, wherein said administration is systemic administration.

* * * * *